(12) United States Patent
Taniguchi et al.

(10) Patent No.: US 10,308,678 B2
(45) Date of Patent: Jun. 4, 2019

(54) CATION EXCHANGE CHROMATOGRAPHIC SUPPORT AND METHOD FOR USING SAME

(71) Applicant: ASAHI KASEI MEDICAL CO., LTD., Tokyo (JP)

(72) Inventors: Hiroki Taniguchi, Tokyo (JP); Ichiro Koguma, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 15/327,161

(22) PCT Filed: Jul. 23, 2015

(86) PCT No.: PCT/JP2015/070950
§ 371 (c)(1),
(2) Date: Jan. 18, 2017

(87) PCT Pub. No.: WO2016/013609
PCT Pub. Date: Jan. 28, 2016

(65) Prior Publication Data
US 2017/0145050 A1    May 25, 2017

(30) Foreign Application Priority Data

Jul. 25, 2014  (JP) .................... 2014-152303
Oct. 15, 2014  (JP) .................... 2014-211112
Dec. 8, 2014   (JP) .................... 2014-248376

(51) Int. Cl.
| | |
|---|---|
| *C07K 1/18* | (2006.01) |
| *C07K 16/00* | (2006.01) |
| *C08J 7/18* | (2006.01) |
| *C08J 9/36* | (2006.01) |
| *G01N 30/02* | (2006.01) |
| *G01N 30/88* | (2006.01) |
| *G01N 30/96* | (2006.01) |
| *B01D 15/36* | (2006.01) |
| *B01D 15/38* | (2006.01) |
| *C07K 1/22* | (2006.01) |
| *C08J 5/22* | (2006.01) |
| *B01J 39/26* | (2006.01) |
| *B01J 47/12* | (2017.01) |
| *B01J 39/19* | (2017.01) |
| *B01J 47/014* | (2017.01) |

(52) U.S. Cl.
CPC .............. *C07K 1/18* (2013.01); *B01D 15/362* (2013.01); *B01D 15/3809* (2013.01); *B01J 39/19* (2017.01); *B01J 39/26* (2013.01); *B01J 47/014* (2017.01); *B01J 47/12* (2013.01); *C07K 1/22* (2013.01); *C07K 16/00* (2013.01); *C08J 5/2243* (2013.01); *C08J 7/18* (2013.01); *C08J 9/36* (2013.01); *G01N 30/02* (2013.01); *G01N 30/88* (2013.01); *G01N 30/96* (2013.01); *C07K 2317/21* (2013.01); *C08J 2323/06* (2013.01)

(58) Field of Classification Search
CPC .......... C07K 1/18; C07K 1/22; B01D 15/362; B01D 15/3809
USPC ....................................................... 502/402
See application file for complete search history.

(56) References Cited

U.S. PATENT DOCUMENTS

| | | |
|---|---|---|
| 2005/0061745 A1 | 3/2005 | Xie et al. |
| 2007/0112178 A1 | 5/2007 | Johansson et al. |
| 2008/0312416 A1 | 12/2008 | Childs et al. |
| 2009/0176052 A1 | 7/2009 | Childs et al. |
| 2010/0181254 A1 | 7/2010 | Graalfs |
| 2013/0056415 A1 | 3/2013 | Kozlov et al. |
| 2013/0225701 A1 | 8/2013 | Soice et al. |
| 2013/0245139 A1 | 9/2013 | Kozlov et al. |
| 2014/0238935 A1 | 8/2014 | Komkova et al. |

FOREIGN PATENT DOCUMENTS

| | | |
|---|---|---|
| CN | 101035602 A | 9/2007 |
| CN | 101678318 A | 3/2010 |
| JP | 2006-519273 A | 8/2006 |
| JP | 2008-508998 A | 3/2008 |
| JP | 2009085933 A | 4/2009 |
| JP | 4776615 B2 | 9/2011 |
| JP | 2012-519065 A | 8/2012 |
| JP | 5234727 B2 | 7/2013 |
| JP | 2013-532829 A | 8/2013 |
| JP | 2013-189427 A | 9/2013 |
| WO | 2014-134147 A1 | 9/2014 |

OTHER PUBLICATIONS

El-Sayed, et al., "Radiation-Initiated Graft Copolymerization of Individual Monomer and Comonomer onto Polyethylene and Polytetrafluoroethylene Films"; Journal of Applied Polymer Science, vol. 39, No. 5; Mar. 5, 1990; pp. 1029-1043.

European Search Report issued in E.P.O. Patent Application No. 15824285.9, dated Jun. 30, 2017.

(Continued)

*Primary Examiner* — Edward M Johnson
(74) *Attorney, Agent, or Firm* — Greenblum & Bernstein, P.L.C.

(57) ABSTRACT

The present invention provides a cation-exchange chromatographic support, comprising a membrane matrix and a copolymer immobilized on the surface of the membrane matrix, wherein the copolymer comprises a (meth)acrylamide-based compound and/or a (meth)acrylate-based compound as monomer units, and the support has one or more species of cation-exchange groups including at least a weak cation-exchange group at a density higher than 30 mmol/L per volume of the support.

30 Claims, 5 Drawing Sheets

(56) References Cited

OTHER PUBLICATIONS

Andrew Coffey, "Optimizing Protein Separations with Agilent Weak Cation-Exchange Columns", Application Note, Agilent technologies, Inc., Dec. 22, 2011 (Dec. 22, 2011), [retrieval date Oct. 8, 2015 (Oct. 8, 2015)], Internet: <URL:http://www.chemagilent.com/pdf/low_5990-9628JAJP.pdf>.
International Search Report issued with respect to Application No. PCT/JP2015/070950, dated Oct. 27, 2015.
International Preliminary Report on Patentability issued with respect to Application No. PCT/JP2015/070950, dated Jan. 31, 2017.

Fig. 3

| | Amount of antibody processed/ membrane volume(mg/mL) | Before processing (content) | | | After processing (content) | | | Monomer recovery rate | Reduction rate of percentage of aggregate |
|---|---|---|---|---|---|---|---|---|---|
| | | Aggregate component(1) | Aggregate component(2) | Monomer component(3) | Aggregate component(1) | Aggregate component(2) | Monomer component(3) | | |
| Example 1 | 410 | 1.54% | 2.20% | 96.25% | 0.04% | 0.29% | 99.67% | 94% | 91% |
| Example 2 | 423 | 1.59% | 1.67% | 96.74% | 0.03% | 0.22% | 99.72% | 80% | 91% |
| Example 3 | 430 | 1.31% | 2.04% | 96.65% | 0.06% | 0.60% | 99.35% | 84% | 81% |
| Example 4 | 345 | 2.49% | 3.19% | 94.32% | 0.46% | 1.27% | 98.27% | 90% | 70% |
| Example 5 | 576 | 3.25% | 2.07% | 94.68% | 0.09% | 0.40% | 99.51% | 90% | 91% |
| Example 6 | 378 | 2.35% | 1.82% | 95.83% | 0.17% | 0.35% | 99.47% | 84% | 87% |
| Example 7 | 517 | 2.12% | 1.56% | 96.32% | 0.00% | 0.26% | 99.74% | 91% | 93% |
| Example 8 | 549 | 3.37% | 1.94% | 94.69% | 0.02% | 0.26% | 99.72% | 89% | 95% |
| Example 9 | 602 | 2.45% | 2.39% | 95.17% | 0.00% | 0.34% | 99.66% | 89% | 93% |
| Example 10 | 1059 | 0.72% | 1.14% | 98.14% | 0.00% | 0.25% | 99.75% | 93% | 87% |
| Example 11 | 945 | 1.57% | 1.55% | 96.88% | 0.11% | 0.41% | 99.49% | 90% | 84% |
| Example 12 | 609 | 2.71% | 2.69% | 94.60% | 0.24% | 0.99% | 98.77% | 90% | 77% |
| Example 13 | 1062 | 2.47% | 1.59% | 95.94% | 0.13% | 0.39% | 99.48% | 92% | 87% |
| Example 14 | 1131 | 2.32% | 2.21% | 95.47% | 0.37% | 1.01% | 98.62% | 89% | 70% |
| Example 15 | 1072 | 1.32% | 2.00% | 96.68% | 0.17% | 0.58% | 99.25% | 85% | 77% |
| Example 16 | 1125 | 1.59% | 2.20% | 96.21% | 0.06% | 0.87% | 99.07% | 90% | 75% |
| Example 17 | 1060 | 1.41% | 1.81% | 96.78% | 0.11% | 0.71% | 99.18% | 93% | 75% |
| Example 18 | 1143 | 2.30% | 2.08% | 95.62% | 0.13% | 0.48% | 99.39% | 88% | 86% |
| Example 19 | 469 | 2.99% | 2.31% | 94.70% | 0.28% | 0.57% | 99.15% | 88% | 84% |
| Example 20 | 502 | 2.48% | 2.24% | 95.29% | 0.18% | 0.58% | 99.29% | 85% | 85% |
| Example 21 | 884 | 2.73% | 2.10% | 95.16% | 0.19% | 0.53% | 99.27% | 89% | 85% |
| Example 22 | 550 | 3.14% | 2.03% | 94.82% | 0.15% | 0.63% | 99.22% | 87% | 86% |
| Example 23 | 901 | 4.41% | 2.16% | 93.43% | 0.39% | 0.52% | 99.09% | 91% | 88% |
| Example 24 | 923 | 2.42% | 1.77% | 95.81% | 0.04% | 0.37% | 99.59% | 87% | 90% |
| Example 25 | 918 | 2.96% | 2.01% | 95.03% | 0.13% | 0.49% | 99.38% | 91% | 88% |
| Example 26 | 931 | 2.83% | 1.96% | 95.21% | 0.04% | 0.41% | 99.55% | 85% | 91% |
| Example 27 | 902 | 2.54% | 1.93% | 95.53% | 0.10% | 0.63% | 99.27% | 90% | 84% |
| Example 28 | 399 | 2.80% | 3.21% | 93.99% | 0.31% | 1.15% | 98.54% | 89% | 78% |
| Example 29 | 379 | 1.77% | 1.86% | 96.44% | 0.07% | 0.32% | 99.52% | 83% | 87% |
| Comparative Example 1 | 410 | 2.27% | 1.86% | 95.87% | 1.76% | 1.17% | 97.07% | 91% | 29% |
| Comparative Example 2 | 959 | 2.03% | 2.06% | 95.91% | 0.98% | 1.31% | 97.71% | 94% | 44% |
| Comparative Example 3 | 412 | 2.12% | 2.31% | 95.57% | 1.78% | 1.91% | 96.31% | 87% | 17% |

Fig. 4

| | | Aggregate component(1) | Aggregate component(2) | Monomer component(3) | HCP | Protein A |
|---|---|---|---|---|---|---|
| Example 30 | Antibody solution | 1.05% | 1.13% | 97.82% | 350ppm | 3ppm |
| | Cation-exchange step: Amount of antibody processed/support volume=1090mg/mL Monomer recovery rate 91% | | | | | |
| | Antibody solution | 0% | 0.18% | 99.82% | 213ppm | 2ppm |
| | Anion-exchange step: Amount of antibody processed/support volume=201mg/mL Monomer recovery rate 96% | | | | | |
| | Antibody solution | 0% | 0.11% | 99.89% | 1ppm | <1ppm |
| Example 31 | Antibody solution | 0.42% | 1.14% | 98.44% | 306ppm | 3ppm |
| | Cation-exchange step: Amount of antibody processed/support volume=314mg/mL Monomer recovery rate 90% | | | | | |
| | Antibody solution | 0.19% | 0.69% | 99.12% | 54ppm | 1ppm |
| | Anion-exchange step: Amount of antibody processed/support volume=930mg/mL Monomer recovery rate 88% | | | | | |
| | Antibody solution | 0% | 0.15% | 99.85% | 1ppm | <1ppm |
| Example 32 | Antibody solution | 0.91% | 1.32% | 97.77% | 390 | 3ppm |
| | Cation-exchange step: Amount of antibody processed/support volume=1067mg/mL Monomer recovery rate 85% | | | | | |
| | Antibody solution | 0.14% | 0.33% | 99.54% | 254ppm | 1ppm |
| | Anion-exchange step: Amount of antibody processed/support volume=4713mg/mL Monomer recovery rate 99% | | | | | |
| | Antibody solution | 0% | 0.21% | 99.79% | 5 | <1ppm |

Fig. 5

| Example 33 | | Aggregate component(1) | Aggregate component(2) | Monomer component(3) | HCP | Protein A |
|---|---|---|---|---|---|---|
| | Antibody solution | 0.72% | 1.04% | 98.24% | 298ppm | 3ppm |
| | Cation-exchange step: Amount of antibody processed/support volume=1204mg/mL Monomer recovery rate 91% ||||||
| | Antibody solution | 0% | 0.16% | 99.84% | 228ppm | 2ppm |
| | Anion-exchange step: Amount of antibody processed/support volume=243mg/mL Monomer recovery rate 97% ||||||
| | Antibody solution | 0% | 0.07% | 99.93% | 2ppm | <1ppm |

| Example 34 | | Aggregate component(1) | Aggregate component(2) | Monomer component(3) | HCP | Protein A |
|---|---|---|---|---|---|---|
| | Antibody solution | 0.83% | 1.12% | 98.05% | 317ppm | 3ppm |
| | Anion-exchange step: Amount of antibody processed/support volume=301mg/mL Monomer recovery rate 95% ||||||
| | Antibody solution | 0.51% | 0.81% | 98.68% | 41ppm | 1ppm |
| | Cation-exchange step: Amount of antibody processed/support volume=1066mg/mL Monomer recovery rate 90% ||||||
| | Antibody solution | 0% | 0.12% | 99.88% | 4ppm | <1ppm |

| Example 35 | | Aggregate component(1) | Aggregate component(2) | Monomer component(3) | HCP | Protein A |
|---|---|---|---|---|---|---|
| | Antibody solution | 0.79% | 1.16% | 98.05% | 390ppm | 3ppm |
| | Cation-exchange step: Amount of antibody processed/support volume=1217mg/mL Monomer recovery rate 91% ||||||
| | Antibody solution | 0% | 0.18% | 99.82% | 287ppm | 2ppm |
| | Anion-exchange step: Amount of antibody processed/support volume=981mg/mL Monomer recovery rate 98% ||||||
| | Antibody solution | 0% | 0.09% | 99.91% | 4ppm | <1ppm |

| Example 36 | | Aggregate component(1) | Aggregate component(2) | Monomer component(3) | HCP | Protein A |
|---|---|---|---|---|---|---|
| | Antibody solution | 0.78% | 1.21% | 98.01% | 365ppm | 3ppm |
| | Anion-exchange step: Amount of antibody processed/support volume=1181mg/mL Monomer recovery rate 97% ||||||
| | Antibody solution | 0.20% | 0.87% | 98.93% | 44ppm | 1ppm |
| | Cation-exchange step: Amount of antibody processed/support volume=1014mg/mL Monomer recovery rate 90% ||||||
| | Antibody solution | 0% | 0.10% | 99.90% | 5ppm | <1ppm |

| Example 37 | | Aggregate component(1) | Aggregate component(2) | Monomer component(3) | HCP | Protein A |
|---|---|---|---|---|---|---|
| | Antibody solution | 0.56% | 1.79% | 97.65% | 349ppm | 4ppm |
| | Cation-exchange step: Amount of antibody processed/support volume=1041mg/mL Monomer recovery rate 95% ||||||
| | Antibody solution | 0% | 0.28% | 99.72% | 279ppm | 1ppm |
| | Anion-exchange step: Amount of antibody processed/support volume=4156mg/mL Monomer recovery rate 99% ||||||
| | Antibody solution | 0% | 0.18% | 99.82% | <1ppm | <1ppm |

| Example 38 | | Aggregate component(1) | Aggregate component(2) | Monomer component(3) | HCP | Protein A |
|---|---|---|---|---|---|---|
| | Antibody solution | 0.99% | 0.98% | 98.03% | 306ppm | 2ppm |
| | Cation-exchange step: Amount of antibody processed/support volume=1145mg/mL Monomer recovery rate 96% ||||||
| | Antibody solution | 0% | 0.10% | 99.90% | 233ppm | <1ppm |
| | Anion-exchange step: Amount of antibody processed/support volume=3734mg/mL Monomer recovery rate 99% ||||||
| | Antibody solution | 0% | 0.07% | 99.93% | 17ppm | <1ppm |

| Example 39 | | Aggregate component(1) | Aggregate component(2) | Monomer component(3) | HCP | Protein A |
|---|---|---|---|---|---|---|
| | Antibody solution | 0.50% | 0.91% | 98.59% | 443ppm | 1ppm |
| | Cation-exchange step: Amount of antibody processed/support volume=1082mg/mL Monomer recovery rate 92% ||||||
| | Antibody solution | 0% | 0.10% | 99.90% | 314ppm | <1ppm |
| | Anion-exchange step: Amount of antibody processed/support volume=894mg/mL Monomer recovery rate 99% ||||||
| | Antibody solution | 0% | 0.07% | 99.93% | 15ppm | <1ppm |

| Example 40 | | Aggregate component(1) | Aggregate component(2) | Monomer component(3) | HCP | Protein A |
|---|---|---|---|---|---|---|
| | Antibody solution | 0.64% | 1.08% | 98.28% | 588ppm | 2ppm |
| | Cation-exchange step: Amount of antibody processed/support volume=1064mg/mL Monomer recovery rate 94% ||||||
| | Antibody solution | 0% | 0.15% | 99.85% | 370ppm | <1ppm |
| | Anion-exchange step: Amount of antibody processed/support volume=874mg/mL Monomer recovery rate 99% ||||||
| | Antibody solution | 0% | 0.08% | 99.92% | 4ppm | <1ppm |

CATION EXCHANGE CHROMATOGRAPHIC SUPPORT AND METHOD FOR USING SAME

TECHNICAL FIELD

The present invention relates to an ion-exchange chromatographic support having a weak cation-exchange group, and a biomolecule purification method using the same.

BACKGROUND ART

Immunoglobulins (antibodies) are physiologically active substances that are responsible for immune response. In recent years, their use values have been increasing in applications such as pharmaceutical products, diagnostic drugs, and materials for separation and purification of corresponding antigenic proteins. The antibodies are obtained from the blood of immunized animals, cell culture solutions of cells possessing the ability to produce antibodies, or ascitic fluid culture solutions of animals. However, such antibody-containing blood or culture solutions contain proteins other than the antibodies, or complicated foreign components derived from stock solutions used in the cell culture. The separation and purification of the antibodies from these impurity components usually require a complicated and time-consuming operation.

Liquid chromatography is important for antibody separation and purification. Examples of chromatography approaches for antibody separation include gel filtration chromatography, affinity chromatography, ion-exchange chromatography, and reverse-phase chromatography. Antibodies are separated and purified by combining these approaches.

The ion-exchange chromatography is a method which involves using ion-exchange groups on the surface of an adsorbent as a stationary phase and reversibly adsorbing thereon counterions present in a mobile phase for separation. For example, beads or a membrane (e.g., flat membranes and hollow fiber) is adopted as the shape of the adsorbent. These matrices bound with cation-exchange groups or anion-exchange groups are commercially available as adsorbents.

Purification using the adsorbent having cation-exchange groups is generally performed by contacting an antibody solution having a low salt concentration with the adsorbent so that antibodies are adsorbed thereon, and eluting the adsorbed physiologically active substances by increasing the salt concentration of a mobile phase. The purification of a substance of interest in a flow-through manner described below has also been proposed as a more favorable method.

The flow-through manner is a manner of a purification method that selectively adsorbs impurities rather than the substance of interest onto an adsorbent. Therefore, this approach leads to a saving in buffer solution and simplification of steps, as compared with conventional methods using adsorption and elution. Also, it is considered that the advantages of the flow-through purification can be further exploited if an antibody solution can be processed at a high flow rate.

A cation-exchange step is often aimed at separating antibody monomers from aggregates such as antibody dimers. However, the antibody monomers and the antibody aggregates have almost equal isoelectric points. Therefore, the separation of antibody monomers from antibody dimers is particularly difficult for the flow-through purification and requires the detailed design of a cation-exchanger, including the density of cation-exchange groups. In addition, each antibody has distinctive properties. Therefore, the same design is not always optimal for all antibodies even if the design is detailed. It is considered that there is a suitable cation-exchange group density for each antibody.

Patent Literature 1 discloses a multimodal chromatographic resin for use in flow-through purification, comprising a resin bound with low-molecular compounds having aromatic and weak cation-exchange groups.

Patent Literature 2 discloses a chromatographic support comprising silica beads bound with copolymers having weak cation-exchange groups.

Patent Literature 3 discloses a chromatographic support suitable for flow-through purification in which monomers having strong cation-exchange groups and uncharged (neutral) monomers are graft-polymerized onto a support.

CITATION LIST

Patent Literature

Patent Literature 1: Japanese Patent No. 4776615
Patent Literature 2: Japanese Patent No. 5234727
Patent Literature 3: Japanese Patent Laid-Open No. 2013-189427

SUMMARY OF INVENTION

Technical Problem

The present inventors have found that the multimodal chromatographic support disclosed in Patent Literature 1 is in a bead form and therefore cannot achieve processing at a high flow rate; thus, the advantages of flow-through purification cannot be exploited.

The present inventors have found that the chromatographic support disclosed in Patent Literature 2, comprising silica beads bound with copolymers cannot achieve processing at a high flow rate.

The cation-exchange membrane disclosed in Patent Literature 3 is characterized by using cation-exchange groups at a low density (1 to 30 mmol/L) on a solid support and is limited by the cation-exchange group density.

Thus, none of the previous literatures disclose a cation-exchanger that allows a charge density to be adjusted in response to the properties of antibodies and is capable of processing at a high flow rate. Thus, an object of the present invention is to provide a cation-exchanger that is capable of processing at a high flow rate in flow-through purification and allows a charge density to be adjusted.

Solution to Problem

The present inventors have conducted studies from various angles and conducted research and development in order to attain the object. As a result, the present inventors have completed the present invention by finding that use of a support bound with a polymer having a weak cation-exchange group permits high-flow rate processing and charge density adjustment and is suitable for the flow-through purification of proteins.

An aspect of the present invention provides a cation-exchange chromatographic support, comprising a membrane matrix and a copolymer immobilized on the surface of the membrane matrix, wherein the copolymer comprises a (meth)acrylamide-based compound and/or a (meth)acrylate-based compound as monomer units, and the support has one or more species of cation-exchange groups including at least a weak cation-exchange group at a density higher than 30 mmol/L per volume of the support.

In the aforementioned cation-exchange chromatographic support, monomer units other than monomer units having the cation-exchange groups in the copolymer may be neutral monomers having no charge, and the neutral monomers may be a hydrophobic monomer unit and/or a hydrophilic monomer unit.

In the aforementioned cation-exchange chromatographic support, the copolymer may comprise at least one species of hydrophobic monomer unit as a monomer unit.

In the aforementioned cation-exchange chromatographic support, the hydrophobic monomer unit may have a linear or branched alkyl group having four or more carbon atoms.

In the aforementioned cation-exchange chromatographic support, the weak cation-exchange group may be derived from any of an acrylic acid monomer, a methacrylic acid monomer, an acrylic acid compound monomer, and a methacrylic acid compound monomer.

In the aforementioned cation-exchange chromatographic support, the weak cation-exchange group may be derived from a methacrylic acid monomer.

In the aforementioned cation-exchange chromatographic support, the mass percentage of the hydrophobic monomer unit and/or the hydrophilic monomer unit in the copolymer may be higher than that of the cation-exchange group-containing monomer units.

In the aforementioned cation-exchange chromatographic support, the one or more species of cation-exchange groups may consist only of weak cation-exchange groups.

In the aforementioned cation-exchange chromatographic support, the one or more species of cation-exchange groups may be a mixture of a weak cation-exchange group and a strong cation-exchange group.

In the aforementioned cation-exchange chromatographic support, the strong cation-exchange group may be a sulfonic acid group.

In the aforementioned cation-exchange chromatographic support, the copolymer may be immobilized on the surface of the membrane matrix through a covalent bond.

In the aforementioned cation-exchange chromatographic support, the copolymer may comprise the (meth)acrylamide-based compound as a hydrophilic monomer unit.

In the aforementioned cation-exchange chromatographic support, the copolymer may comprise isopropylacrylamide as a hydrophilic monomer unit.

In the aforementioned cation-exchange chromatographic support, the copolymer may comprise the (meth)acrylate-based compound as a hydrophilic monomer unit.

In the aforementioned cation-exchange chromatographic support, the copolymer may comprise 2-hydroxyethyl methacrylate as a hydrophilic monomer unit.

In the aforementioned cation-exchange chromatographic support, the membrane matrix may comprise polyethylene.

In the aforementioned cation-exchange chromatographic support, the graft ratio of the copolymer graft-polymerized onto the membrane matrix may be 20 to 200%.

In the aforementioned cation-exchange chromatographic support, the membrane matrix may be polyvinylidene fluoride.

In the aforementioned cation-exchange chromatographic support, the graft ratio of the copolymer graft-polymerized onto the membrane matrix may be 5 to 100%.

In the aforementioned cation-exchange chromatographic support, the copolymer substantially may have no cross-linked structure.

In the aforementioned cation-exchange chromatographic support, the copolymer may comprise a monomer unit containing two or more polymerizable functional groups.

In the aforementioned cation-exchange chromatographic support, the polymerizable functional groups may be derived from (meth)acrylamide or (meth)acrylate.

The aforementioned cation-exchange chromatographic support may be a cation-exchange chromatographic support for biomolecule purification. The biomolecule may be an antibody.

The aforementioned cation-exchange chromatographic support may reduce the percentage of aggregates by 50% or more when 100 mg of antibodies including monomers and the aggregates is flow-through purified with respect to 1 mL of the support.

Another aspect of the present invention provides a purification method for purifying a physiologically active substance from a mixed solution containing impurities and the physiologically active substance, the purification method comprising contacting the mixed solution with the aforementioned cation-exchange chromatographic support to obtain the physiologically active substance with improved purity.

The aforementioned purification method is based on a flow-through technique.

In the aforementioned purification method, the recovery rate of the physiologically active substance may be 80% or more.

In the aforementioned purification method, the physiologically active substance may be a monomer of an antibody protein.

In the aforementioned purification method, the impurities may include dimer or higher aggregates of the antibody protein.

In the aforementioned purification method, purification using an anion-exchange chromatographic support may be performed before or after the purification step with the cation-exchange chromatographic support.

In the aforementioned purification method, the anion-exchange chromatographic support may be in a membrane-like form.

In the aforementioned purification method, the anion-exchange chromatographic support may have a structure having a graft polymer on a matrix.

In the aforementioned purification method, the purification with the anion-exchange chromatographic support may be based on a flow-through technique.

In the aforementioned purification method, buffer replacement may not be performed between the purification step with the cation-exchange chromatographic support and the purification step with the anion-exchange chromatographic support.

In the aforementioned purification method, the purification step with the cation-exchange chromatographic support and the purification step with the anion-exchange chromatographic support may be continuously performed.

In the aforementioned purification method, the hydrogen ion exponent of the buffer may be changed by the addition of an acid or a base between the purification step with the cation-exchange chromatographic support and the purification step with the anion-exchange chromatographic support.

The aforementioned purification method may further comprise the step of changing an electric conductivity by 0.01 mS/cm or larger between the purification step with the cation-exchange chromatographic support and the purification step with the anion-exchange chromatographic support.

The aforementioned purification method may further comprise a purification step by affinity chromatography before the purification step with the cation-exchange chromatographic support.

In the aforementioned purification method, buffer replacement may not be performed after elution of the physiologically active substance in the affinity chromatography step.

In the aforementioned purification method, the elution buffer for use in the elution of the physiologically active substance in the affinity chromatography step may be composed mainly of a monovalent acid.

In the aforementioned purification method, the elution buffer for use in the elution of the physiologically active substance in the affinity chromatography step may be an acetate buffer.

In the aforementioned purification method, the elution buffer for use in the elution of the physiologically active substance in the affinity chromatography step may have an electric conductivity of 10 mS/cm or lower.

In the aforementioned purification method, virus inactivation may be performed by acidic treatment after the affinity chromatography step.

Advantageous Effects of Invention

Use of the cation-exchange chromatographic support according to the present invention permits high-flow rate processing and further achieves protein purification at a charge density in response to the properties of proteins.

BRIEF DESCRIPTION OF DRAWINGS

FIG. 3 is a table showing results of Examples 1 to 29 and Comparative Examples 1 to 3.

FIG. 4 is a table showing results of Examples 30 to 32.

FIG. 5 is a table showing results of Examples 33 to 40.

DESCRIPTION OF EMBODIMENTS

Figure 1:
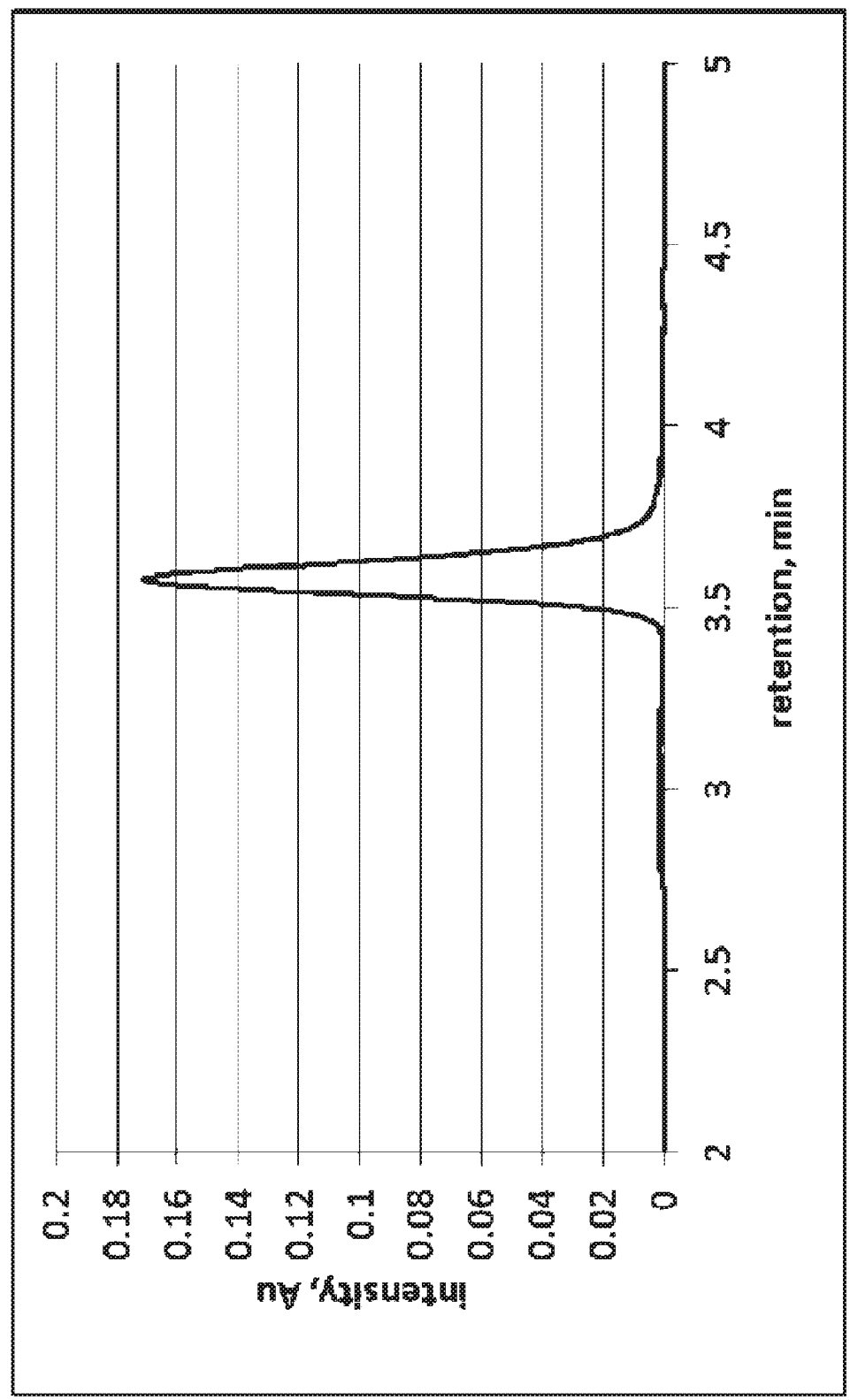
FIG. 1 is a graph of absorbance when an antibody solution according to Example 1 was applied to size exclusion chromatography.

Hereinafter, preferred embodiments (hereinafter, referred to as "embodiments") of the present invention will be described in detail. The embodiments shown below are given for illustrating apparatuses or methods for concretizing the technical idea of this invention. The technical idea of this invention does not limit combinations of constituent members, etc., to those described below. The technical idea of this invention can be variously changed or modified within the scope of claims.

The cation-exchange chromatographic support according to an embodiment comprises a membrane matrix and a copolymer immobilized on the surface of the membrane matrix, wherein the copolymer comprises a (meth)acrylamide-based compound and/or a (meth)acrylate-based compound as monomer units, and the support has one or more species of cation-exchange groups including at least a weak cation-exchange group at a density higher than 30 mmol/L, preferably a density higher than 40 mmol/L, more preferably a density higher than 45 mmol/L, per volume of the support.

The "(meth)acrylamide-based compound" is a monomer or a monomer unit having acrylamide as a backbone and may be hydrophilic or hydrophobic depending on a structure other than the backbone. The "(meth)acrylate-based compound" is a monomer or a monomer unit having acrylate as a backbone and may be hydrophilic or hydrophobic depending on a structure other than the backbone.

The "density" means the concentration of cation-exchange groups in the cation-exchange chromatographic support, and this concentration is generally indicated as the concentration in terms of the number of moles of cation-exchange groups per liter of the cation-exchange chromatographic support. The "cation" is also referred to as a positive ion, and the "anion" is also referred to as a negative ion. The "support" is also referred to as an exchanger, an adsorbent, or a stationary phase.

The cation-exchange chromatographic support according to an embodiment is used, for example, for the purification of a physiologically active substance. The physiologically active substance is, for example, a monomer component of an antibody protein. The impurities are, for example, dimer or higher aggregates of the antibody protein.

The antibody protein, which is one example of the physiologically active substance, is a glycoprotein molecule (also referred to as a gamma globulin or an immunoglobulin) that is produced by B lymphocytes in the infection protection mechanism of vertebrates as generally defined in biochemistry. For example, the antibody protein purified with the cation-exchange chromatographic support according to an embodiment is used as a drug for humans and has substantially the same structure as that of the in vivo antibody proteins of humans as recipients.

The antibody protein may be a human antibody protein or may be an antibody protein derived from a non-human mammal (e.g. cattle and a mouse). Alternatively, the antibody protein may be a chimeric antibody protein with human IgG or a humanized antibody protein. The chimeric antibody protein with human IgG is an antibody protein having variable regions derived from a non-human organism such as a mouse and additionally having constant regions replaced with those of a human-derived immunoglobulin. The humanized antibody protein is an antibody protein having a non-human organism-derived complementarity-determining regions (CDRs) in variable regions and additionally having human-derived framework regions (FRs). The humanized antibody protein has much lower immunogenicity than that of the chimeric antibody protein.

The antibody protein, which is one example of a subject to be purified with the cation-exchange chromatographic support according to an embodiment, is not particularly limited by its class (isotype) and subclass. Antibody proteins are classified into, for example, five families of classes, IgG, IgA, IgM, IgD, and IgE, according to difference in constant region structure. However, the antibody protein to be purified with the cation-exchange chromatographic support according to an embodiment may be any of these five families of classes. Human antibody proteins have four IgG subclasses, IgG1 to IgG4, and two IgA subclasses, IgA1 and IgA2. However, the antibody protein to be purified with the cation-exchange chromatographic support according to an embodiment may be any of the subclasses. Antibody-related proteins such as Fc fusion proteins composed of a Fc region bound with a protein can also be included in the antibody protein to be purified with the cation-exchange chromatographic support according to an embodiment.

Antibody proteins can also be further classified depending on their origins. However, the antibody protein to be purified with the cation-exchange chromatographic support according to an embodiment may be any of natural human antibody proteins, recombinant human antibody proteins produced by a gene recombination technique, monoclonal antibody proteins, and polyclonal antibody proteins. Among these antibody proteins, human IgG is preferred as the antibody protein to be purified with the cation-exchange chromatographic support according to an embodiment from the viewpoint of a demand and importance as an antibody drug, though the antibody protein is not limited thereto.

The membrane matrix comprised in the cation-exchange chromatographic support according to an embodiment is not particularly limited by its shape. Examples of the shape include hollow fiber, flat membranes, nonwoven cloth, monoliths, capillaries, sintered compacts, discs, and cylinders. The material is not particularly limited and is preferably constituted by a polyolefin-based polymer, a polyamide (nylon), a polyester, polyethersulfone, cellulose, or the like.

Examples of the polyolefin-based polymer include: olefin homopolymers such as ethylene, propylene, butylene, and vinylidene fluoride; copolymers of two or more of the olefins; and copolymers of one or two or more of the olefins and a perhalogenated olefin. Examples of the perhalogenated olefin include tetrafluoroethylene and/or chlorotrifluoroethylene. Among them, polyethylene or polyvinylidene fluoride is preferred from the viewpoint of having excellent mechanical strength and producing high adsorption capacity of impurities such as proteins. Examples of the polyamide include, but are not particularly limited to, nylon 6 (ε-caprolactam polycondensate), nylon 11 (undecanelactam polycondensate), nylon 12 (lauryllactam polycondensate), nylon 66 (copolycondensate of hexamethylenediamine and adipic acid), nylon 610 (copolycondensate of hexamethylenediamine and adipic acid), nylon 6T (copolycondensate of hexamethylenediamine and terephthalic acid), nylon 9T (copolycondensate of nonanediamine and terephthalic acid), nylon M5T (copolycondensate of methylpentanediamine and terephthalic acid), nylon 621 (copolycondensate of caprolactam and lauryllactam), copolycondensates of p-phenylenediamine and terephthalic acid, and copolycondensates of m-phenylenediamine and isophthalic acid. Examples of the polyester include, but are not particularly limited to, polyethylene terephthalate, polytrimethylene terephthalate, polybutylene terephthalate, polyethylene naphthalate, and polybutylene naphthalate.

The membrane matrix has, for example, a plurality of pores. The pore size is not particularly limited and is, for example, 5 to 1000 nm, preferably 10 nm or larger, more preferably 50 nm or larger, further preferably 100 nm or larger, particularly preferably 150 nm or larger or 400 nm or larger, for a matrix in a hollow fiber form. Also, the pore size is preferably 900 nm or smaller, more preferably 800 nm or smaller, further preferably 700 nm or smaller, particularly preferably 650 nm or smaller from the viewpoint of the surface area of a membrane matrix. A membrane matrix having a pore size of 5 nm or smaller tends to be able to separate antibody proteins having a smaller molecular weight. Also, a membrane matrix having a pore size of 1000 nm or larger has a smaller surface area and tends to have a smaller binding capacity of impurities.

When a graft ratio mentioned later is high or when the percentage of hydrophilic monomers in the copolymer is high, the pores of a hollow fiber membrane tend to be clogged. In such a case, a pore size on the order of 400 to 650 nm is particularly preferred.

When the matrix is in a flat membrane form or in a nonwoven cloth form, the preferred range of the pore size is increased because it is possible to use a backing material or it is possible to laminate such matrices for using the matrix as a membrane. The preferred range is 10 nm to 1 mm, preferably 100 nm or larger, more preferably 200 nm or larger, further preferably 300 nm or larger. Also, the preferred range is preferably 500 um or smaller, more preferably 300 um or smaller, further preferably 100 um or smaller, from the viewpoint of a surface area.

The cation-exchange chromatographic support according to an embodiment has at least a weak cation-exchange group and has one or more species of cation-exchange groups at a density higher than 30 mmol/L per volume of the support.

Examples of the weak cation-exchange group include a carboxylic acid group, a phosphonic acid group, and a phosphoric acid group. The weak cation-exchange group can vary in charge quantity depending on the pH of a mobile phase. Therefore, the charge density of the cation-exchange chromatographic support can be adjusted by changing the pH of a mobile phase.

The method for introducing the weak cation-exchange group includes a method of copolymerizing monomers having the weak cation-exchange group. Examples of such monomers include acrylic acid, methacrylic acid, acrylic acid compounds, and methacrylic acid compounds. Examples of the acrylic acid compounds include 2-acryloxyethylsuccinic acid, 2-acryloxyethylhexahydrophthalic acid, and 2-acryloxyethylphthalic acid. Examples of the methacrylic acid compounds include 2-methacryloxyethylsuccinic acid, 2-methacryloxyethylhexahydrophthalic acid, and 2-methacryloxyethylphthalic acid.

The weak cation-exchange group may be introduced by copolymerizing monomers having a group convertible to the weak cation-exchange group, followed by functional group conversion. Such a functional group is an ester or the like. Examples of the monomers include monomers such as t-butyl acrylate, t-butyl methacrylate, benzyl acrylate, benzyl methacrylate, allyl acrylate, and allyl methacrylate. These monomers are used in the copolymerization, and then, the group can be deprotected under acidic conditions and converted to a carboxylic acid group.

The cation-exchange chromatographic support according to an embodiment may have a strong cation-exchange group as long as having at least one species of weak cation-exchange group, or may only have the weak cation-exchange group without having a strong cation-exchange group. The total density of cation-exchange groups can be higher than 30 mmol/L per volume of the support.

The introduction of the strong cation-exchange group can render change in charge quantity insensitive to pH and improve reproducibility. Almost all of strong cation-exchange groups have a charge in a pH region of a practical antibody solution in antibody purification and therefore have a constant charge quantity. Thus, the presence of the strong cation-exchange group in the cation-exchange chromatographic support secures a constant charge quantity equal to or larger than a given level. The charge quantity of the weak cation-exchange group can be adjusted by changing pH so that the charge quantity of the whole cation-exchange chromatographic support can be finely adjusted. The presence of the strong cation-exchange group in the cation-exchange chromatographic support can prevent the performance of the cation-exchange chromatographic support from depending largely on small change in pH. Examples of the strong cation-exchange group include a sulfonic acid group.

A total density of cation-exchange groups lower than 30 mmol/L tends to decrease the amount of cation-exchange groups that may be charged, reduce adsorption capacity, and lower the amount of antibodies that can be processed. In Patent Literature 3, the selectivity of flow-through purification between antibody monomers and aggregates is exerted by using strong cation-exchange groups and setting the density of cation-exchange groups to 30 mmol/L or lower.

However, such a low density decreases adsorption capacity and lowers the amount of antibodies that can be processed. A density of cation-exchange groups equal to or lower than 30 mmol/L tends to narrow a possible charge quantity range and narrow the families of applicable antibodies.

The total density of cation-exchange groups per volume of the support can be higher than 30 mmol/L. When the density of weak cation-exchange groups among these cation-exchange groups is 5 mol/L or higher, preferably 10 mol/L or higher, more preferably 15 mmol/L or higher, it is possible to adjust the charge density.

The copolymer comprised in the cation-exchange chromatographic support according to an embodiment is immobilized on the membrane matrix. The copolymer is immobilized on the membrane matrix, for example, through a covalent bond. This support has at least a weak cation-exchange group and can finally have one or more species of cation-exchange groups at a density higher than 30 mmol/L.

The method for immobilizing the copolymer onto the membrane matrix includes graft polymerization. Examples of the graft polymerization method include radiation graft polymerization and surface living radical polymerization methods.

In the case of immobilizing the copolymer onto the surface of the membrane matrix by the radiation graft polymerization method, any approach may be adopted for generating radicals on the membrane matrix. The irradiation of the membrane matrix with ionizing radiation generates homogeneous radicals throughout the membrane matrix and is therefore preferred. For example, β ray, electron ray, β ray, and neutron ray can be used as the species of the ionizing radiation. Electron ray or γ ray is preferred for industrial-scale execution. The ionizing radiation is obtained from a radioisotope such as cobalt 60, strontium 90, or cesium 137 or using an X-ray photography apparatus, an electron beam accelerator, an ultraviolet irradiation apparatus, or the like.

The irradiation dose of the ionizing radiation is preferably 1 kGy or larger and 1000 kGy or smaller, more preferably 2 kGy or larger and 500 kGy or smaller, further preferably 5 kGy or larger and 200 kGy or smaller. An irradiation dose of smaller than 1 kGy tends to be less likely to generate homogeneous radicals. Also, an irradiation dose exceeding 1000 kGy tends to cause reduction in the physical strength of the membrane matrix.

In general, graft polymerization methods based on irradiation with ionizing radiation are broadly classified into: a preirradiation method which involves generating radicals on the membrane matrix and subsequently contacting the radicals with reactive compounds; and a simultaneous irradiation method which involves generating radicals on the membrane matrix with the membrane matrix contacted with reactive compounds. Any method may be applied to this embodiment, and the preirradiation method is preferred which rarely forms oligomers.

The solvent for use in the polymerization for the copolymer according to an embodiment is not particularly limited as long as the solvent can uniformly dissolve the reactive compounds. Examples of such a solvent include: alcohols such as methanol, ethanol, isopropanol, and t-butyl alcohol; ethers such as diethyl ether and tetrahydrofuran; ketones such as acetone and 2-butanone; water; and mixtures thereof.

The copolymer comprises, in its composition, one or more species of monomer units selected from compounds of acrylamides, methacrylamides, acrylates, and methacrylates in addition to monomer units having the cation-exchange groups. The copolymer may consist only of any combination of acrylamides, methacrylamides, acrylates, and methacrylates or may consist only of methacrylates. The copolymer may further comprise, in its composition, one or more species of hydrophilic and/or hydrophobic compounds, which are neutral monomers having no charge, as monomer units. These monomer units tend to be stable against practical acidic or basic conditions for washing the cation-exchange chromatography, be less likely to undergo reduction in performance caused by washing, and be less likely to reduce membrane strength. It is considered that these hydrophilic and/or hydrophobic monomers are copolymerized with the monomers having the cation-exchange groups so that the distance between the cation-exchange groups is widened and more selective adsorption of antibody aggregates is facilitated. Examples of an additional monomer unit include acrylonitrile. However, acrylonitrile is easily hydrolyzed by an alkali. Therefore, acrylonitrile, when used as a monomer unit, is not preferred because its performance tends to be impaired by alkali washing. Monomer units containing an aromatic group, such as styrenes, are not preferred because these monomer units tend to render the membrane stiff and fragile. The mass percentage of the hydrophilic monomer unit and/or the hydrophobic monomer unit as neutral monomers in the copolymer is preferably higher than, more preferably twice or more, further preferably three or more times that of the monomer units having the cation-exchange from the viewpoint of differentiating adsorption power for antibody monomers from adsorption power for antibody aggregates.

In an embodiment, the copolymer consists only of a cation-exchange group-containing monomer and a neutral monomer. Therefore, the mass of the cation-exchange group-containing monomer and the mass of the neutral monomer can be determined as follows:

(Mass of the cation-exchange group-containing monomer)=(Cation-exchange group density–Support volume×Molecular weight of the cation-exchange group-containing monomer)

(Mass of the neutral monomer)=(Mass of the cation-exchange support–Mass of the matrix support–Mass of the cation-exchange group-containing monomer)

The mass percentage of the cation-exchange group-containing monomer unit and the mass percentage of the neutral monomer unit can be determined from these mass ratios.

Since antibodies have properties based on hydrophobic interaction, the antibodies may be adsorbed onto a membrane matrix through hydrophobic interaction resulting from the strong hydrophobicity of the membrane matrix. As a result, the recovery rate of an antibody of interest may be reduced. In order to cope with this phenomenon, the adsorption of antibodies onto the membrane matrix can be prevented by introducing a hydrophilic monomer during the polymerization for the copolymer. Examples of such a hydrophilic monomer include acrylamide, methacrylamide, and (meth)acrylamide compounds such as dimethylacrylamide, dimethylmethacrylamide, diethylacrylamide, diethylmethacrylamide, N-methylacrylamide, N-methylmethacrylamide, N-ethylacrylamide, N-ethylmethacrylamide, N-isopropylacrylamide, N-isopropylmethacrylamide, N-(hydroxymethyl)acrylamide, N-(hydroxymethyl)methacrylamide, N-(2-hydroxyethyl)acrylamide, and N-(2-hydroxyethyl)methacrylamide. Alternatively, examples of the hydrophilic monomer as described above include acrylate, methacrylate, and (meth)acrylate compounds such as 2-hydroxyethyl acrylate, 2-hydroxyethyl methacrylate, 3-hydroxypropyl acrylate, 3-hydroxypropyl methacrylate, 4-hydroxybutyl acrylate, 4-hydroxybutyl methacrylate, 2-(dimethylamino)ethyl acrylate, and 2-(dimethylamino) ethyl methacrylate.

Alternatively, the adsorption selectivity between antibody monomers and antibody aggregates may be enhanced by introducing a hydrophobic monomer during the polymerization for the copolymer and thereby exploiting the hydrophobic interaction. In general, antibody aggregates exhibit stronger hydrophobic interaction than that of antibody monomers. The selection of a suitable hydrophobic monomer can achieve the marked difference in hydrophobic interaction between antibody monomers and antibody aggregates and high selectivity. Examples of such a hydrophobic monomer include styrenes, alkylacrylamides, alkylmethacrylamides, alkyl acrylates, and alkyl methacrylates. Alkylacrylamides, alkylmethacrylamides, alkyl acrylates, and alkyl methacrylates are desirable from the viewpoint of dynamic strength. The alkyl group can be any linear or branched alkyl group having four or more carbon atoms, and the resulting monomer can substantially cause hydrophobic interaction with antibodies.

The copolymer may neither comprise a monomer unit containing two or more polymerizable functional groups nor may have a cross-linked structure. Alternatively, the copolymer may comprise a monomer unit containing two or more polymerizable functional groups and may have a cross-linked structure. However, preferably, the copolymer substantially has a non-cross-linked structure. The substantially non-cross-linked copolymer refers to a copolymer having a low degree of cross-linking that does not substantially influence antibody aggregate adsorption performance even if having a cross-linked structure. When the copolymer is substantially non-cross-linked, the mass percentage of the monomer unit containing two or more polymerizable functional groups is, for example, 10% or lower, 5% or lower, 4% or lower, 3% or lower, 2% or lower, 1% or lower, 0.5% or lower, or 0.1% or lower. A lower mass percentage thereof is more preferred.

Examples of the monomer containing two or more polymerizable functional groups include, but are not particularly limited to, monomers having olefins as the polymerizable functional groups. Examples of such a monomer include (meth)acrylamide-based monomers, (meth)acrylate-based monomers, and monomers having a mixture of their functional groups. Examples of the (meth)acrylamide-based monomers include N,N'-methylenebisacrylamide, N,N'-ethylenebisacrylamide, N,N'-propylenebisacrylamide, N,N'-(1,2-dihydroxyethylene)bisacrylamide, N,N'-methylenebismethacrylamide, N,N'-ethylenebismethacrylamide, N,N'-propylenebismethacrylamide, and N,N'-(1,2-dihydroxyethylene)bismethacrylamide.

Examples of the (meth)acrylate-based monomers include ethylene glycol diacrylate, 1,3-butanediol diacrylate, 1,4-butanediol diacrylate, 1,5-pentanediol diacrylate, 1,6-hexanediol diacrylate, 1,9-nonanediol diacrylate, 1,10-decanediol diacrylate, neopentyl glycol diacrylate, diethylene glycol diacrylate, triethylene glycol diacrylate, polyethylene glycol diacrylate, dipropylene glycol diacrylate, tripropylene glycol diacrylate, 2-hydroxy-1,3-propanediol diacrylate, 4,4'-thiodibenzenethiol diacrylate, trimethylolpropane triacrylate, pentaerythritol tetraacrylate, ethylene glycol dimethacrylate, 1,3-butanediol dimethacrylate, 1,4-butanediol dimethacrylate, 1,5-pentanediol dimethacrylate, 1,6-hexanediol dimethacrylate, 1,9-nonanediol dimethacrylate, 1,10-decanediol dimethacrylate, neopentyl glycol dimethacrylate, diethylene glycol dimethacrylate, triethylene glycol dimethacrylate, polyethylene glycol dimethacrylate, dipropylene glycol dimethacrylate, tripropylene glycol dimethacrylate, 2-hydroxy-1,3-propanediol dimethacrylate, 4,4'-thiodibenzenethiol dimethacrylate, trimethylolpropane trimethacrylate, and pentaerythritol tetramethacrylate.

The optimum value of the graft chain binding ratio (graft ratio) of the graft polymerization may differ depending on the density of the membrane matrix. When the membrane matrix is polyethylene, the graft ratio is preferably 20% or more, more preferably 25% or more, further preferably 30% or more, from the viewpoint of adsorption capacity. Also, the graft ratio is preferably 200% or less, more preferably 150% or less, further preferably 100% or less, from the viewpoint of securing dynamically stable strength. The graft ratio is represented by the following expression:

$$dg(\%) = (w1-w0)/w0 \times 100$$

wherein w0 represents the weight of the porous hollow fiber before reaction, and w1 represents the weight of the graft chain-introduced porous hollow fiber.

When the membrane matrix is polyvinylidene fluoride, the suitable graft ratio differs from that of polyethylene because polyvinylidene fluoride has a higher density than that of polyethylene. When the membrane matrix is polyvinylidene fluoride, the graft ratio is preferably 5% or more, more preferably 10% or more, further preferably 15% or more, from the viewpoint of adsorption capacity. Also, the graft ratio is preferably 100% or less, more preferably 80% or less, further preferably 70% or less, from the viewpoint of securing dynamically stable strength.

The cation-exchange group-containing copolymer immobilized on the membrane matrix permits steric adsorption as compared with cation-exchange groups distributed on the surface of the membrane matrix. Therefore, antibody aggregates are more strongly adsorbed on the matrix than antibody monomers so that the antibody monomers can be obtained with high purity. Thus, the copolymer preferably has at least a weak cation-exchange group and has one or more species of cation-exchange groups. A copolymer having a cross-linked structure interferes with the steric adsorption of antibody aggregates onto the matrix, though this copolymer has the advantage that the pressure of a passing liquid is reduced by suppressing the rising of the copolymer. Therefore, it is desirable that the copolymer should substantially have a non-cross-linked structure, from the viewpoint of more strongly adsorbing antibody aggregates than antibody monomers so that the antibody monomers can be obtained with high purity.

If the copolymer contains a small amount of hydrophilic monomers, this copolymer is elongated or contracted and makes it impossible to sterically adsorb antibody aggregates. Therefore, the steric adsorption of antibody aggregates requires a content thereof above a certain level. The mass percentage of the hydrophilic monomers in such a copolymer is preferably 30% or more, more preferably 40% or more, further preferably 50% or more, particularly preferably 60% or more. It is desirable that the mass percentage of the hydrophilic monomers should be higher than that of hydrophobic monomers. The mass percentage of the hydrophilic monomers is preferably 1.3 or more times, more preferably 1.5 or more times, further preferably 1.7 or more times, particularly preferably 1.9 or more times that of the hydrophobic monomers. The mass percentages of the hydrophilic monomers and the hydrophobic monomers can be detected from the final product by pyrolysis GC/MS. Alternatively, these mass percentages can also be calculated, assuming that the mass percentages agree with mixing composition ratios for synthesis. For the graft polymerization, the mass ratio of the hydrophilic monomers corresponds to the weight ratio of the hydrophilic monomers to all monomers mixed.

The method for determining the total cation-exchange group density also includes a method which involves protonating all of the cation-exchange groups using a strong acid or the like, followed by neutralization using a base and measurement by back titration. Another method involves replacing counter cations of the cation-exchange groups with lithium ions, followed by treatment with a strong acid and the measurement of the amount of lithium eluted. The total cation-exchange group density can be measured by these methods.

The method for measuring the strong cation-exchange group density can involve, for example, protonating all of the strong cation-exchange groups using a strong acid or the like, followed by the addition of an aqueous sodium chloride solution and the titration of eluted hydrogen chloride for measurement.

The weak cation-exchange group density can be determined by subtracting the strong cation-exchange group density from the total cation-exchange group density.

The purification method for obtaining a physiologically active substance with improved purity according to an embodiment is a purification method for purifying the physiologically active substance from a mixed solution containing impurities and the physiologically active substance, the purification method comprising contacting the mixed solution with the aforementioned cation-exchange chromatographic support. The recovery rate of the physiologically active substance by the purification method according to an embodiment is, for example, 80% or more. The recovery rate is calculated according to the following expression:

Recovery rate=(Amount of antibodies recovered×Monomer component purity after the processing)/(Amount of antibodies processed×Monomer component purity before the processing)

The flow-through (purification) refers to a purification method aimed at allowing a physiologically active substance of interest to flow through the material. For example, when a monomer of an antibody protein is a material of interest and aggregates of an antibody protein are impurities, the antibody protein monomer flows through the adsorbent whereas the antibody protein aggregates bind to the adsorbent. In this respect, the antibody protein monomer may be adsorbed onto the adsorbent, but is purified by the more selective adsorption of the antibody protein aggregates onto the adsorbent.

The chromatographic mobile phase in flow-through purification using the cation-exchange support according to an embodiment can employ a buffer solution (buffer) other than a strong acid and a strong alkali, and some mobile phases do not require an organic solvent. In this context, the buffer solution is an aqueous solution containing a salt. Specific examples thereof include phosphate buffer solutions, tris buffer solutions, and acetate buffer solutions. The buffer solution is not particularly limited as long as the buffer solution is usually used. The concentration of the salt is 0 to 100 mmol/L, preferably 0 to 50 mmol/L, more preferably 0 to 30 mmol/L. The buffer concentration is 1 to 100 mmol/L, preferably 2 to 70 mmol/L, more preferably 5 to 50 mmol/L. In this context, the buffer concentration refers to the concentration of an active ingredient in the buffer. For example, the acetate buffer is usually prepared from acetic acid and sodium acetate, and the buffer concentration of the acetate buffer is the total concentration of acetic acid and sodium acetate. The buffer concentration of the tris buffer refers to the concentration of trishydroxymethylaminomethane. The buffer concentration of a buffer indicated by an acetate-tris buffer or the like is the concentration of the former component. The buffer concentration of acetate-tris is the concentration of acetate while the buffer concentration of tris-acetate is the concentration of tris. In the present embodiment, a solution of pH hardly having buffering ability (e.g., an acetate buffer solution of pH 3.4) can also be used in the chromatography.

A concentration of an inorganic salt higher than 100 mmol/L in the buffer solution tends to reduce the degree of dissociation of ion-exchange groups and make it difficult to carry impurities such as aggregates.

The concentration of the salt is indicated by preferably 0.5 to 20 mS/cm, more preferably 0.5 to 15 mS/cm, further preferably 0.5 to 10 mS/cm, particularly preferably 0.8 to 5.0 mS/cm, with an electric conductivity as an index.

The hydrogen ion concentration of the buffer solution differs depending on the isoelectric point, size, etc., of antibody proteins to be processed, and the optimum conditions need to be appropriately studied. The pH is, for example, 4.0 to 10.0, preferably 5.0 to 9.5, more preferably 6.0 to 9.0, particularly preferably 6.5 to 8.0. pH near the isoelectric point of antibody proteins tends to decrease the electrostatic repulsion between antibody proteins, which are easily aggregated. Also, pH of lower than 4.0 tends to denature antibody proteins and cause reduction in activity or reduction in quality such as the purification of aggregates.

The amount of antibodies loaded in the cation-exchange chromatography step is not particularly limited as long as impurities can be removed. The amount of antibodies loaded is 100 mg or larger per mL of the support and is preferably 300 mg or larger, more preferably 500 mg or larger, further preferably 700 mg or larger, still further preferably 0.8 g or larger, particularly preferably 1 g or larger, per mL of the support from the viewpoint of efficient purification.

The cation-exchange chromatography step that is carried out in the present embodiment reduces the percentage of antibody aggregates in antibodies by 50% or more, more preferably 60% or more, further preferably 70% or more, when 100 mg or larger of antibodies including monomers and the aggregates is flow-through purified with respect to 1 mL of the support. The reduction rate of the percentage of antibody aggregates is indicated by percentage of a value obtained by dividing the difference of the content of the aggregate components (1) and (2) after the processing from the content of the aggregate components (1) and (2) before the processing by the content of the aggregate components (1) and (2) before the processing. The respective contents of the aggregate components (1) and (2) are calculated from peak areas in a chromatographic chart.

The purification step by cation-exchange chromatography that is carried out in the present embodiment can be combined with an anion-exchange chromatography step to thereby further improve the purity of a purified product.

In a purification step with a conventional general cation-exchange chromatographic support, a substance of interest is temporarily adsorbed onto the support and purified by elution. Therefore, impurities having pI higher than that of the substance of interest and impurities having pI lower than that of the substance of interest can both be removed. On the other hand, the flow-through purification of the present embodiment may have a difficulty in removing impurities having pI lower than that of the substance of interest. However, the impurities having pI lower than that of the substance of interest can be removed by purification with an anion-exchange chromatographic support. Therefore, the purification step with the cation-exchange chromatographic support according to the present embodiment can be combined with a purification step with an anion-exchange chromatographic support to thereby achieve efficient purification while maintaining the conventional property of removing impurities.

Examples of the impurities having pI lower than that of the substance of interest include, but are not particularly limited to, host cell-derived protein (HCP), DNA, and protein A, which is an impurity derived from an affinity chromatography step.

The purification step with an anion-exchange chromatographic support may be performed before or after the purification step with the cation-exchange chromatographic support.

The anion-exchange chromatographic support is not particularly limited, and any anion-exchange chromatographic support in a membrane-like form permits a high flow rate and achieves construction of a more efficient purification step. The anion-exchange chromatographic support may also have a structure having a graft polymer chain on a matrix.

The structure of the anion-exchange chromatographic support is not particularly limited, and any structure having a graft polymer on a matrix can sterically adsorb impurities and can therefore be expected to have the higher property of removing impurities.

The purification method with the anion-exchange chromatographic support is not particularly limited, and flow-through purification achieves more efficient purification.

The amount of antibodies loaded in the anion-exchange chromatography step is not particularly limited as long as impurities can be removed. The amount of antibodies loaded is preferably 0.2 g or larger, more preferably 0.5 g or larger, further preferably 1.0 g or larger, still further preferably 2.0 g or larger, particularly preferably 4 g or larger, per mL of the support from the viewpoint of efficient purification.

Buffer replacement may or may not be performed between the purification step with the cation-exchange chromatographic support and the purification step with the anion-exchange chromatographic support. Without buffer replacement, more efficient purification can be performed.

The purification step with the cation-exchange chromatographic support and the purification step with the anion-exchange chromatographic support may be continuously performed, or a purified product may be temporarily stored in a tank after the completion of a preceding step and then subjected to the next step.

pH adjustment may be performed between the purification step with the cation-exchange chromatographic support and the purification step with the anion-exchange chromatographic support. The pH adjustment enhances the property of removing impurities having pI around the pH of the former processing. Specifically, in the case of first performing the purification with the cation-exchange chromatographic support, the pH is increased by the addition of a base before the purification with the anion-exchange chromatographic support so that a larger amount of impurities can be removed. On the other hand, in the case of first using the anion-exchange chromatographic support, the pH is decreased by the addition of an acid before the purification with the cation-exchange chromatographic support so that a larger amount of impurities can be removed. The pH value to be changed is not particularly limited as long as the property of removing impurities is improved. The pH can be arbitrarily changed according to the target impurities. Examples of the value of the amount of change in pH include 0.01, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, and 3.0. The presented values themselves or any value between these values may be selected.

Preferably, the property of removing impurities is particularly improved by changing the pH by 0.1 or more, though this value is not particularly limited as long as impurities can be removed.

As with the pH, electric conductivity adjustment may be performed between the purification step with the cation-exchange chromatographic support and the purification step with the anion-exchange chromatographic support. The electric conductivity value to be changed is not particularly limited as long as the property of removing impurities is improved. The electric conductivity can be arbitrarily changed according to the target impurities. Examples of the value of the amount of change in electric conductivity include 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, and 5.0. The presented values themselves or any value between these values may be selected.

In general antibody purification, purification is performed in an ion-exchange chromatography step after purification by affinity chromatography. In the present embodiment, an affinity chromatography step may be performed before the purification step by cation-exchange chromatography and the anion-exchange chromatography step. The flow-through purification by cation-exchange chromatography and the anion-exchange chromatography step as described above can be performed after the affinity chromatography step to obtain a more highly pure material of interest.

According to the present embodiment, efficient purification is achieved by performing the flow-through purification by cation-exchange chromatography and the flow-through purification by anion-exchange chromatography without buffer replacement of an antibody-containing eluate after the affinity chromatography step. Such an eluting solution includes a buffer composed mainly of a monovalent acid.

In a general anion-exchange chromatography step, use of an elution buffer composed mainly of a polyvalent acid tends to reduce the amount of substances adsorbed and reduce the property of removing impurities. Therefore, for using an elution buffer composed mainly of a polyvalent acid in an affinity chromatography step, it is desirable that the buffer should be replaced before anion-exchange chromatography. However, provided that elution in the affinity chromatography step is performed using an elution buffer composed mainly of a monovalent acid, purification by the cation-exchange chromatography step and the anion-exchange chromatography step can be performed without the need of buffer replacement.

The elution buffer composed mainly of a monovalent acid is not particularly limited as long as elution is achieved in the affinity chromatography step and impurities can be removed in a subsequent ion-exchange chromatography step. An acetate buffer is desirable.

The elution buffer for use in the elution in the affinity chromatography step has, but not particularly limited to, an electric conductivity of desirably 10.0 mS/cm or lower, more preferably 7.0 mS/cm or lower, further preferably 5.0 mS/cm or lower, particularly preferably 3.0 mS/cm or lower, from the viewpoint of the property of removing impurities in the subsequent flow-through purification by cation-exchange chromatography.

For maintaining the electric conductivity of an elution pool low, it is desirable that the support should be washed with a buffer solution having a low electric conductivity immediately before elution in the affinity chromatography step. The buffer solution can have sufficiently high pH and a sufficiently low electric conductivity so as not to elute antibodies.

Such pH is preferably 5.0 or higher, more preferably 6.0 or higher, further preferably 7.0 or higher, and such electric conductivity is preferably 10.0 mS/cm or lower, more preferably 7.0 mS/cm or lower, further preferably 5.0 mS/cm or lower, particularly preferably 3.0 mS/cm or lower.

After the elution in the affinity chromatography step, virus inactivation may be performed by exposing viruses that may be contained in the eluate to acidic (low pH) conditions for a given time. For the virus inactivation, pH is desirably 4.0 or lower, preferably 3.8 or lower, more preferably 3.6 or lower, further preferably 3.5 or lower, particularly preferably 3.4 or lower.

After the affinity chromatography step or the subsequent virus inactivation, the pH of the eluate may be adjusted by the addition of a base to the eluate. The value of the pH thus adjusted is not particularly limited as long as impurities can be removed in a subsequent ion-exchange chromatography step. The value of the adjust pH is preferably 4.0 or higher, more preferably 5.0 or higher, further preferably 6.0 or higher.

EXAMPLES

Hereinafter, the embodiments will be described further specifically with reference to Examples. However, the embodiments are not intended to be limited by these examples by any means.

Example 1

In Example 1, a cation-exchange membrane in a hollow fiber form having carboxylic acid groups was synthesized by the radiation graft polymerization method.

1) Radiation Graft Polymerization 3.09 g of N-isopropylacrylamide, 1.54 g of butyl methacrylate, and 0.51 g of methacrylic acid were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 200 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 5.31 g of a cation-exchange membrane having a graft ratio of 77%.

The volume of one filament of the obtained hollow fiber was measured and was consequently 1.05 mL. This hollow fiber was hydrophilized with ethanol, followed by replacement with water. After removal of water, 10 mL of a 0.1 mol/L aqueous sodium hydroxide solution was added to the hollow fiber. The hollow fiber was left for 1 hour, and then, the aqueous sodium hydroxide solution was isolated, followed by the addition of 10 mL of pure water. The hollow fiber was further left for 1 hour, and then, sodium hydroxide remaining in the membrane was recovered by recovering pure water. The recovered sodium hydroxide solutions were combined and titrated using 0.1 mol/L hydrochloric acid. As a result, 7.98 mL was required for neutralization. The blank was 9.77 mL, revealing that sodium hydroxide-reacted weak cation-exchange groups carried by the membrane were 179 umol. This value can be divided by the measured volume to determine a weak cation-exchange group density. The cation-exchange group density was 170 mmol/L. The resultant was made into a module (membrane volume: 0.25 mL) to prepare cation-exchange membrane 1 according to Example 1. The mass percentages of cation-exchange group-containing monomers and neutral monomers were 0.100 and 0.900, respectively.

2) Preparation of Cell Culture Solution

A culture supernatant containing 0.115 g/L AE6F4 antibodies (human monoclonal antibodies) as antibody proteins was prepared. AE6F4-producing cells were kindly provided by associate professor Yoshinori Katakura (Faculty of Agriculture, Kyushu University). The AE6F4 antibody-producing cells were cultured with reference to the literature (Proceedings of Annual Meeting of The Society for Biotechnology, Japan, 1994, Vol. 65, p. 65). The culture solution containing the AE6F4 antibody-producing cells was filtered through a filtration membrane (manufactured by Asahi Kasei Medical Co., Ltd., trade name: BioOptimal® MF-SL) to obtain an antibody solution (culture supernatant) containing impurities and the antibodies. The filtration was carried out with reference to the instruction manual of the distributor.

3) Purification of Antibody Protein with Protein a Column

2 L of the filtered antibody solution was added to a protein A column (manufactured by GE Healthcare Biosciences Corp., packed with MabSelect Sure) equilibrated with 150 mL of a phosphate buffer solution (20 mmol/L sodium phosphate+150 mmol/L NaCl (pH 8.0)) so that the antibody proteins were adsorbed onto protein A. Next, the column was washed by passing 20 mL of a phosphate buffer solution (20 mmol/L sodium phosphate+150 mmol/L NaCl (pH 8.0)). Then, the antibody proteins were eluted from the protein A column by passing 240 mL of an elution buffer solution (100 mmol/L sodium citrate (pH 3.6)) to the column to recover an antibody solution with impurities reduced to some extent.

4) Preparation of Aggregate

A portion of the obtained antibody solution was adjusted to pH 3 by the addition of hydrochloric acid and left for 1 hour. Then, the solution was neutralized using an aqueous sodium hydroxide solution to prepare an antibody solution containing a large amount of aggregates.

5) Preparation of Antibody Solution Containing Aggregate

The antibody solution obtained from the protein A column was buffer-replaced with a 15 mmol/L tris buffer solution (pH 7.0), and the resulting solution was mixed with a solution obtained by the buffer replacement of the antibody solution containing a large amount of aggregates with a 15 mmol/L tris buffer solution (pH 7.0), at an arbitrary ratio to prepare an antibody solution containing aggregates.

6) Measurement of Amount of Aggregate

The obtained antibody solution was measured using a size exclusion chromatography (SEC) apparatus under the following conditions:

Column: ACQUITY YPLC BEH200 SEC 1.7 um (manufactured by Waters Corp.)

Column temperature: 30° C.

System: ACQUITY UPLC H CLASS (manufactured by Waters Corp.)

Mobile phase: aqueous solution of 0.1 mol/L disodium hydrogen phosphate+0.2 mol/L L(+)-arginine (adjusted to pH 6.7 with hydrochloric acid)

Figure 2:
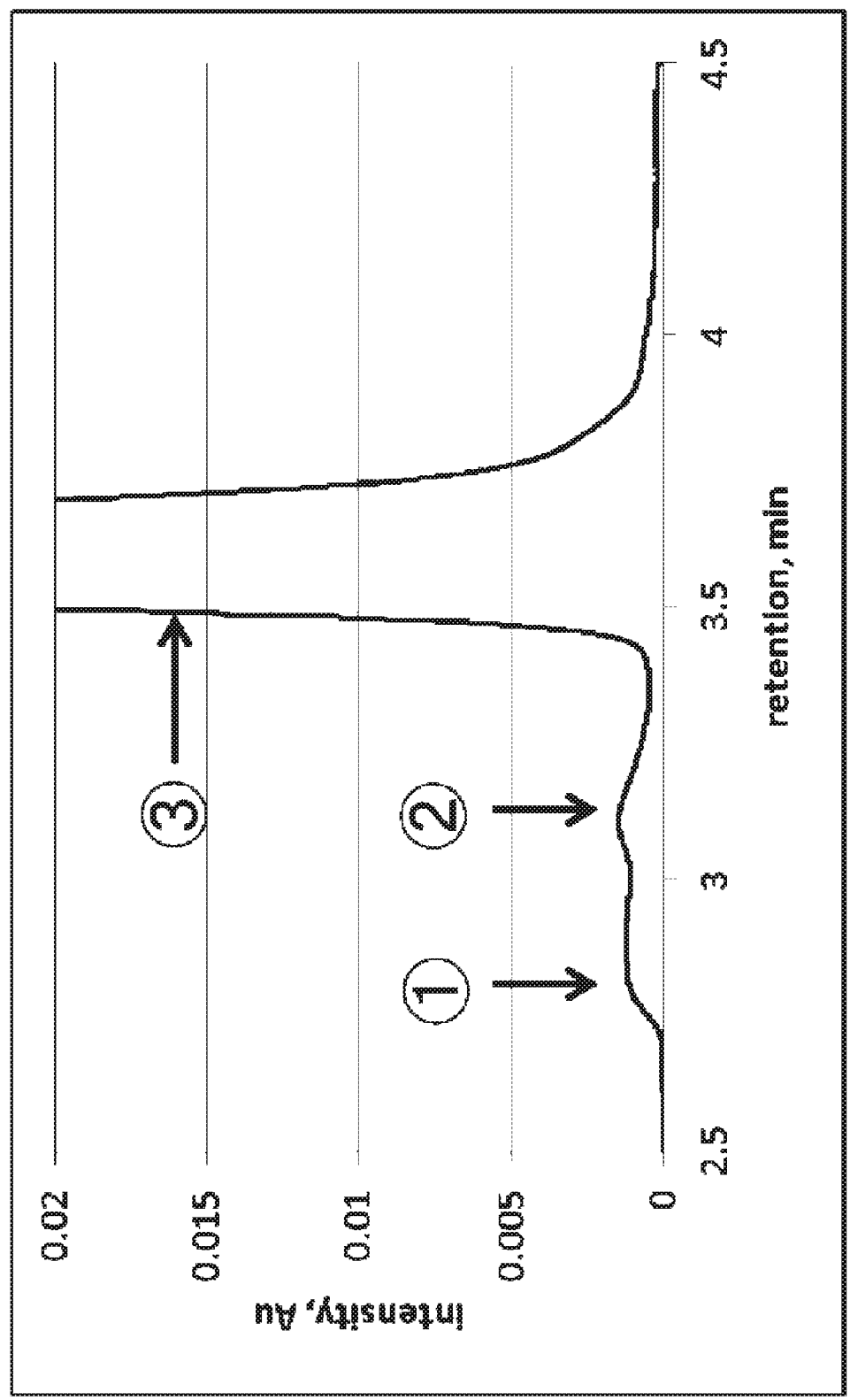
FIG. 2 is an enlarged view of the graph of FIG. 1.

As a result, the chromatographic chart of FIG. 1 was obtained. An enlarged view of this chart is shown in FIG. 2. Peaks (1) and (2) in FIG. 2 depict antibody aggregates, and peak (3) depicts monomers. The percentage of the aggregates (1) calculated from the peak area of the chromatographic chart was 1.54%, the percentage of the aggregates (2) was 2.20%, and the percentage of the monomers was 96.25%. In Examples and Comparative Examples below, the first appearing peak of aggregates is referred to as aggregates (1), and the second appearing peak of aggregates is referred to as aggregates (2).

7) Removal of Aggregate

The antibody solution containing aggregate components (impurities) and monomer components (physiologically active substance of interest) of the antibody proteins was contacted with cation-exchange membrane 1. The amount of the antibody solution added was 20 mL (concentration: 5.12 mg/mL), the flow rate was 1.5 mL/min, and the temperature was 25° C. After the flowing of the antibody solution, cation-exchange membrane 1 was washed with 10 mL of a 15 mmol/L tris buffer solution (pH 7.0) of 25° C. flowing at a flow rate of 1.5 mL/min. 30 mL of a solution was recovered by the flow-through step and the washing step. The recovered solution was applied to size exclusion chromatography (SEC). As a result, the content of the aggregate components was decreased. The results are shown in FIG. 3. In FIG. 3, "Reduction rate of percentage of aggregate" is indicated by percentage of a value obtained by dividing the difference of the content of the aggregate components (1) and (2) after the processing from the content of the aggregate components (1) and (2) before the processing by the content of the aggregate components (1) and (2) before the processing.

Example 2

In Example 2, cation-exchange membrane 2 described below was used. Cation-exchange membrane 2 was synthesized as follows: 3.09 g of N-isopropylacrylamide, 1.03 g of butyl methacrylate, and 1.03 g of methacrylic acid were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 200 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 5.32 g of a cation-exchange membrane having a graft ratio of 77%. The cation-exchange group density measured in the same way as in Example 1 was 390 mmol/L. The resultant was made into a module (membrane volume: 0.25 mL) to prepare cation-exchange membrane 2 according to Example 2. The mass percentages of cation-exchange group-containing monomers and neutral monomers were 0.217 and 0.783, respectively.

In the antibody solution used in Example 2, the percentage of the aggregates (1) was 1.59%, the percentage of the aggregates (2) was 1.67%, and the percentage of the monomers was 96.74%.

The antibody solution containing aggregate components (impurities) and monomer components (physiologically active substance of interest) of the antibody proteins was contacted with cation-exchange membrane 2. The amount of the antibody solution added was 20 mL (concentration: 5.29 mg/mL), the flow rate was 1.5 mL/min, and the temperature was 25° C. After the flowing of the antibody solution, cation-exchange membrane 2 was washed with 10 mL of a 15 mmol/L tris buffer solution (pH 7.0) of 25° C. flowing at a flow rate of 1.5 mL/min. 30 mL of a solution was recovered by the flow-through step and the washing step. The recovered solution was applied to size exclusion chromatography (SEC). As a result, the content of the aggregate components was decreased. The results are shown in FIG. 3.

Example 3

In Example 3, cation-exchange membrane 3 described below was used. Cation-exchange membrane 3 was synthesized as follows: 3.09 g of N-isopropylacrylamide, 1.77 g of butyl methacrylate, and 0.28 g of methacrylic acid were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 200 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 5.17 g of a cation-exchange membrane having a graft ratio of 72%. The cation-exchange group density measured in the same way as in Example 1 was 59 mmol/L. The resultant was made into a module (membrane volume: 0.25 mL) to prepare cation-exchange membrane 3 according to Example 3. The mass percentages of cation-exchange group-containing monomers and neutral monomers were 0.035 and 0.965, respectively.

The antibody solution used in Example 3 was a 15 mmol/L tris buffer solution (pH 8.0). The percentage of the aggregates (1) was 1.31%, the percentage of the aggregates (2) was 2.04%, and the percentage of the monomers was 96.66%.

The antibody solution containing aggregate components (impurities) and monomer components (physiologically active substance of interest) of the antibody proteins was contacted with cation-exchange membrane 3. The amount of the antibody solution added was 20 mL (concentration: 5.37 mg/mL), the flow rate was 1.5 mL/min, and the temperature was 25° C. After the flowing of the antibody solution, cation-exchange membrane 3 was washed with 10 mL of a 15 mmol/L tris buffer solution (pH 8.0) of 25° C. flowing at a flow rate of 1.5 mL/min. 30 mL of a solution was recovered by the flow-through step and the washing step. The recovered solution was applied to size exclusion chromatography (SEC). As a result, the content of the aggregate components was decreased. The results are shown in FIG. 3.

Example 4

In Example 4, cation-exchange membrane 3 and an antibody solution described below were used. The antibody solution used in Example 4 was a 15 mmol/L tris buffer solution (pH 9.0). The percentage of the aggregates (1) was 2.49%, the percentage of the aggregates (2) was 3.19%, and the percentage of the monomers was 94.32%.

The antibody solution containing aggregate components (impurities) and monomer components (physiologically active substance of interest) of the antibody proteins was contacted with cation-exchange membrane 3. The amount of the antibody solution added was 20 mL (concentration: 4.31 mg/mL), the flow rate was 1.5 mL/min, and the temperature was 25° C. After the flowing of the antibody solution, cation-exchange membrane 3 was washed with 10 mL of a 15 mmol/L tris buffer solution (pH 9.0) of 25° C. flowing at a flow rate of 1.5 mL/min. 30 mL of a solution was recovered by the flow-through step and the washing step. The recovered solution was applied to size exclusion chromatography (SEC). As a result, the content of the aggregate components was decreased. The results are shown in FIG. 3.

Example 5

In Example 5, cation-exchange membrane 4 described below was used. Cation-exchange membrane 4 was synthesized as follows: 3.83 g of N-isopropylacrylamide, 1.92 g of butyl methacrylate, and 0.64 g of methacrylic acid were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 25 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 5.32 g of a cation-exchange membrane having a graft ratio of 77%. The cation-exchange group density measured in the same way as in Example 1 was 183 mmol/L. The resultant was made into a module (membrane volume: 0.25 mL) to prepare cation-exchange membrane 4 according to Example 5. The mass percentages of cation-exchange group-containing monomers and neutral monomers were 0.102 and 0.898, respectively.

The antibody solution used in Example 5 was a 15 mmol/L tris buffer solution (pH 7.0). The percentage of the aggregates (1) was 3.25%, the percentage of the aggregates (2) was 2.07%, and the percentage of the monomers was 94.68%.

The antibody solution containing aggregate components (impurities) and monomer components (physiologically active substance of interest) of the antibody proteins was contacted with cation-exchange membrane 4. The amount of the antibody solution added was 25 mL (concentration: 5.76 mg/mL), the flow rate was 1.5 mL/min, and the temperature was 25° C. After the flowing of the antibody solution, cation-exchange membrane 4 was washed with 10 mL of a 15 mmol/L tris buffer solution (pH 7.0) of 25° C. flowing at a flow rate of 1.5 mL/min. 35 mL of a solution was recovered by the flow-through step and the washing step. The recovered solution was applied to size exclusion chromatography (SEC). As a result, the content of the aggregate components was decreased. The results are shown in FIG. 3.

Example 6

In Example 6, cation-exchange membrane 5 described below was used. Cation-exchange membrane 5 was synthesized as follows: 1.49 g of 2-hydroxyethyl methacrylate, 0.72 g of butyl methacrylate, and 0.36 g of methacrylic acid were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 200 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 4.35 g of a cation-exchange membrane having a graft ratio of 45%. The cation-exchange group density measured in the same way as in Example 1 was 155 mmol/L. The resultant was made into a module (membrane volume: 0.25 mL) to prepare cation-exchange membrane 5 according to Example 6. The mass percentages of cation-exchange group-containing monomers and neutral monomers were 0.148 and 0.852, respectively.

The antibody solution used in Example 6 was a 15 mmol/L tris buffer solution (pH 7.0). The percentage of the aggregates (1) was 2.35%, the percentage of the aggregates (2) was 1.82%, and the percentage of the monomers was 95.83%.

The antibody solution containing aggregate components (impurities) and monomer components (physiologically active substance of interest) of the antibody proteins was contacted with cation-exchange membrane 5. The amount of the antibody solution added was 20 mL (concentration: 4.73 mg/mL), the flow rate was 1.5 mL/min, and the temperature was 25° C. After the flowing of the antibody solution, cation-exchange membrane 5 was washed with 10 mL of a 15 mmol/L tris buffer solution (pH 7.0) of 25° C. flowing at a flow rate of 1.5 mL/min. 30 mL of a solution was recovered by the flow-through step and the washing step. The recovered solution was applied to size exclusion chromatography (SEC). As a result, the content of the aggregate components was decreased. The results are shown in FIG. 3.

Example 7

In Example 7, cation-exchange membrane 6 described below was used. Cation-exchange membrane 6 was synthesized as follows: 2.06 g of 2-hydroxyethyl methacrylate, 1.03 g of butyl methacrylate, and 0.51 g of methacrylic acid were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 200 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 4.72 g of a cation-exchange membrane having a graft ratio of 57%. The cation-exchange group density measured in the same way as in Example 1 was 178 mmol/L. The resultant was made into a module (membrane volume: 0.25 mL) to prepare cation-exchange membrane 6 according to Example 7. The mass percentages of cation-exchange group-containing monomers and neutral monomers were 0.134 and 0.866, respectively.

The antibody solution used in Example 7 was a 15 mmol/L tris buffer solution (pH 7.0). The percentage of the aggregates (1) was 2.12%, the percentage of the aggregates (2) was 1.56%, and the percentage of the monomers was 96.32%.

The antibody solution containing aggregate components (impurities) and monomer components (physiologically active substance of interest) of the antibody proteins was contacted with cation-exchange membrane 6. The amount of the antibody solution added was 25 mL (concentration: 5.17 mg/mL), the flow rate was 1.5 mL/min, and the temperature was 25° C. After the flowing of the antibody solution, cation-exchange membrane 6 was washed with 10 mL of a 15 mmol/L tris buffer solution (pH 7.0) of 25° C. flowing at a flow rate of 1.5 mL/min. 35 mL of a solution was recovered by the flow-through step and the washing step. The recovered solution was applied to size exclusion chromatography (SEC). As a result, the content of the aggregate components was decreased. The results are shown in FIG. 3.

Example 8

In Example 8, cation-exchange membrane 7 described below was used. Cation-exchange membrane 7 was synthesized as follows: 2.57 g of 2-hydroxyethyl methacrylate, 1.29 g of butyl methacrylate, and 0.51 g of methacrylic acid were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 200 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 5.28 g of a cation-exchange membrane having a graft ratio of 76%. The cation-exchange group density measured in the same way as in Example 1 was 177 mmol/L. The resultant was made into a module (membrane volume: 0.25 mL) to prepare cation-exchange membrane 7 according to Example 8. The mass percentages of cation-exchange group-containing monomers and neutral monomers were 0.100 and 0.900, respectively.

The antibody solution used in Example 8 was a 15 mmol/L tris buffer solution (pH 7.0). The percentage of the aggregates (1) was 3.37%, the percentage of the aggregates (2) was 1.94%, and the percentage of the monomers was 94.69%.

The antibody solution containing aggregate components (impurities) and monomer components (physiologically active substance of interest) of the antibody proteins was contacted with cation-exchange membrane 7. The amount of the antibody solution added was 25 mL (concentration: 5.49 mg/mL), the flow rate was 1.5 mL/min, and the temperature was 25° C. After the flowing of the antibody solution, cation-exchange membrane 7 was washed with 10 mL of a 15 mmol/L tris buffer solution (pH 7.0) of 25° C. flowing at a flow rate of 1.5 mL/min. 35 mL of a solution was recovered by the flow-through step and the washing step. The recovered solution was applied to size exclusion chromatography (SEC). As a result, the content of the aggregate components was decreased. The results are shown in FIG. 3.

Example 9

In Example 9, cation-exchange membrane 8 described below was used. Cation-exchange membrane 8 was synthesized as follows: 2.57 g of 2-hydroxyethyl methacrylate, 1.29 g of butyl methacrylate, and 0.51 g of methacrylic acid were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 25 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 4.97 g of a cation-exchange membrane having a graft ratio of 66%. The cation-exchange group density measured in the same way as in Example 1 was 174 mmol/L. The resultant was made into a module (membrane volume: 0.25 mL) to prepare cation-exchange membrane 8 according to Example 9. The mass percentages of cation-exchange group-containing monomers and neutral monomers were 0.114 and 0.886, respectively.

The antibody solution used in Example 9 was a 15 mmol/L tris buffer solution (pH 7.0). The percentage of the aggregates (1) was 2.45%, the percentage of the aggregates (2) was 2.39%, and the percentage of the monomers was 95.17%.

The antibody solution containing aggregate components (impurities) and monomer components (physiologically active substance of interest) of the antibody proteins was contacted with cation-exchange membrane 8. The amount of the antibody solution added was 25 mL (concentration: 6.02 mg/mL), the flow rate was 1.5 mL/min, and the temperature was 25° C. After the flowing of the antibody solution, cation-exchange membrane 8 was washed with 10 mL of a 15 mmol/L tris buffer solution (pH 7.0) of 25° C. flowing at a flow rate of 1.5 mL/min. 35 mL of a solution was recovered by the flow-through step and the washing step. The recovered solution was applied to size exclusion chromatography (SEC). As a result, the content of the aggregate components was decreased. The results are shown in FIG. 3.

Example 10

In Example 10, cation-exchange membrane 9 described below was used. Cation-exchange membrane 9 was synthesized as follows: 2.40 g of 2-hydroxyethyl methacrylate, 1.20 g of butyl methacrylate, and 0.77 g of methacrylic acid were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 25 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 4.82 g of a cation-exchange membrane having a graft ratio of 61%. The cation-exchange group density measured in the same way as in Example 1 was 249 mmol/L. The resultant was made into a module (membrane volume: 0.25 mL) to prepare cation-exchange membrane 9 according to Example 10. The mass percentages of cation-exchange group-containing monomers and neutral monomers were 0.177 and 0.823, respectively.

The antibody solution used in Example 10 was a 15 mmol/L tris buffer solution (pH 7.0). The percentage of the aggregates (1) was 0.72%, the percentage of the aggregates (2) was 1.14%, and the percentage of the monomers was 98.14%.

The antibody solution containing aggregate components (impurities) and monomer components (physiologically active substance of interest) of the antibody proteins was contacted with cation-exchange membrane 9. The amount of the antibody solution added was 50 mL (concentration: 5.30 mg/mL), the flow rate was 1.5 mL/min, and the temperature was 25° C. After the flowing of the antibody solution, cation-exchange membrane 9 was washed with 10 mL of a 15 mmol/L tris buffer solution (pH 7.0) of 25° C. flowing at a flow rate of 1.5 mL/min. 60 mL of a solution was recovered by the flow-through step and the washing step. The recovered solution was applied to size exclusion chromatography (SEC). As a result, the content of the aggregate components was decreased. The results are shown in FIG. 3.

Example 11

In Example 11, cation-exchange membrane 10 described below was used. Cation-exchange membrane 10 was synthesized as follows: 3.08 g of 2-hydroxyethyl methacrylate, 1.54 g of butyl methacrylate, and 0.57 g of methacrylic acid were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 25 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 5.31 g of a cation-exchange membrane having a graft ratio of 77%. The cation-exchange group density measured in the same way as in Example 1 was 175 mmol/L. The resultant was made into a module (membrane volume: 0.25 mL) to prepare cation-exchange membrane 10 according to Example 11. The mass percentages of cation-exchange group-containing monomers and neutral monomers were 0.103 and 0.897, respectively.

The antibody solution used in Example 11 was a 15 mmol/L tris buffer solution (pH 7.0). The percentage of the aggregates (1) was 1.57%, the percentage of the aggregates (2) was 1.55%, and the percentage of the monomers was 96.88%.

The antibody solution containing aggregate components (impurities) and monomer components (physiologically active substance of interest) of the antibody proteins was contacted with cation-exchange membrane 10. The amount of the antibody solution added was 40 mL (concentration: 5.91 mg/mL), the flow rate was 1.5 mL/min, and the temperature was 25° C. After the flowing of the antibody solution, cation-exchange membrane 10 was washed with 10 mL of a 15 mmol/L tris buffer solution (pH 7.0) of 25° C. flowing at a flow rate of 1.5 mL/min. 50 mL of a solution was recovered by the flow-through step and the washing step. The recovered solution was applied to size exclusion chromatography (SEC). As a result, the content of the aggregate components was decreased. The results are shown in FIG. 3.

Example 12

In Example 12, cation-exchange membrane 11 described below was used. Cation-exchange membrane 11 was synthesized as follows: 1.93 g of 2-hydroxyethyl methacrylate, 1.93 g of butyl methacrylate, and 0.51 g of methacrylic acid were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 25 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 5.06 g of a cation-exchange membrane having a graft ratio of 69%. The cation-exchange group density measured in the same way as in Example 1 was 177 mmol/L. The resultant was made into a module (membrane volume: 0.25 mL) to prepare cation-exchange membrane 11 according to Example 12. The mass percentages of cation-exchange group-containing monomers and neutral monomers were 0.11 and 0.89, respectively.

The antibody solution used in Example 12 was a 15 mmol/L tris buffer solution (pH 7.0). The percentage of the aggregates (1) was 2.71%, the percentage of the aggregates (2) was 2.69%, and the percentage of the monomers was 94.60%.

The antibody solution containing aggregate components (impurities) and monomer components (physiologically active substance of interest) of the antibody proteins was contacted with cation-exchange membrane 11. The amount of the antibody solution added was 30 mL (concentration: 5.08 mg/mL), the flow rate was 1.5 mL/min, and the temperature was 25° C. After the flowing of the antibody solution, cation-exchange membrane Y was washed with 10 mL of a 15 mmol/L tris buffer solution (pH 7.0) of 25° C. flowing at a flow rate of 1.5 mL/min. 40 mL of a solution was recovered by the flow-through step and the washing step. The recovered solution was applied to size exclusion chromatography (SEC). As a result, the content of the aggregate components was decreased. The results are shown in FIG. 3.

Example 13

In Example 13, cation-exchange membrane 10 and an antibody solution described below were used. The antibody solution used in Example 13 was a 15 mmol/L tris buffer solution (pH 7.0) containing 10 mmol/L sodium chloride. The percentage of the aggregates (1) was 2.47%, the percentage of the aggregates (2) was 1.59%, and the percentage of the monomers was 95.94%.

The antibody solution containing aggregate components (impurities) and monomer components (physiologically active substance of interest) of the antibody proteins was contacted with cation-exchange membrane 10. The amount of the antibody solution added was 50 mL (concentration: 5.31 mg/mL), the flow rate was 1.5 mL/min, and the temperature was 25° C. After the flowing of the antibody solution, cation-exchange membrane 10 was washed with 10 mL of a 15 mmol/L tris buffer solution (pH 7.0) containing 10 mmol/L sodium chloride of 25° C. flowing at a flow rate of 1.5 mL/min. 60 mL of a solution was recovered by the flow-through step and the washing step. The recovered solution was applied to size exclusion chromatography (SEC). As a result, the content of the aggregate components was decreased. The results are shown in FIG. 3.

Example 14

In Example 14, cation-exchange membrane 10 and an antibody solution described below were used. The antibody solution used in Example 14 was a 15 mmol/L tris buffer solution (pH 7.0) containing 30 mmol/L sodium chloride. The percentage of the aggregates (1) was 2.32%, the percentage of the aggregates (2) was 2.21%, and the percentage of the monomers was 95.47%.

The antibody solution containing aggregate components (impurities) and monomer components (physiologically active substance of interest) of the antibody proteins was contacted with cation-exchange membrane 10. The amount of the antibody solution added was 50 mL (concentration: 5.66 mg/mL), the flow rate was 1.5 mL/min, and the temperature was 25° C. After the flowing of the antibody solution, cation-exchange membrane 10 was washed with 10 mL of a 15 mmol/L tris buffer solution (pH 7.0) containing 30 mmol/L sodium chloride of 25° C. flowing at a flow rate of 1.5 mL/min. 60 mL of a solution was recovered by the flow-through step and the washing step. The recovered solution was applied to size exclusion chromatography (SEC). As a result, the content of the aggregate components was decreased. The results are shown in FIG. 3.

Example 15

In Example 15, cation-exchange membrane 10 and an antibody solution described below were used. The antibody solution used in Example 15 was a 15 mmol/L tris buffer solution (pH 7.5). The percentage of the aggregates (1) was 1.32%, the percentage of the aggregates (2) was 2.00%, and the percentage of the monomers was 96.68%.

The antibody solution containing aggregate components (impurities) and monomer components (physiologically active substance of interest) of the antibody proteins was contacted with cation-exchange membrane 10. The amount of the antibody solution added was 50 mL (concentration: 5.36 mg/mL), the flow rate was 1.5 mL/min, and the temperature was 25° C. After the flowing of the antibody solution, cation-exchange membrane 10 was washed with 10 mL of a 15 mmol/L tris buffer solution (pH 7.5) of 25° C. flowing at a flow rate of 1.5 mL/min. 60 mL of a solution was recovered by the flow-through step and the washing step. The recovered solution was applied to size exclusion chromatography (SEC). As a result, the content of the aggregate components was decreased. The results are shown in FIG. 3.

Example 16

In Example 16, cation-exchange membrane 10 and an antibody solution described below were used. The antibody solution used in Example 16 was a 15 mmol/L tris buffer solution (pH 7.5) containing 10 mmol/L sodium chloride. The percentage of the aggregates (1) was 1.59%, the percentage of the aggregates (2) was 2.20%, and the percentage of the monomers was 96.21%.

The antibody solution containing aggregate components (impurities) and monomer components (physiologically active substance of interest) of the antibody proteins was contacted with cation-exchange membrane 10. The amount of the antibody solution added was 50 mL (concentration: 5.63 mg/mL), the flow Late was 1.5 mL/min, and the temperature was 25° C. After the flowing of the antibody solution, cation-exchange membrane 10 was washed with 10 mL of a 15 mmol/L tris buffer solution (pH 7.5) containing 10 mmol/L sodium chloride of 25° C. flowing at a flow rate of 1.5 mL/min. 60 mL of a solution was recovered by the flow-through step and the washing step. The recovered solution was applied to size exclusion chromatography (SEC). As a result, the content of the aggregate components was decreased. The results are shown in FIG. 3.

Example 17

In Example 17, cation-exchange membrane 10 and an antibody solution described below were used. The antibody solution used in Example 17 was a 15 mmol/L tris buffer solution (pH 8). The percentage of the aggregates (1) was 1.41%, the percentage of the aggregates (2) was 1.81%, and the percentage of the monomers was 96.78%.

The antibody solution containing aggregate components (impurities) and monomer components (physiologically active substance of interest) of the antibody proteins was contacted with cation-exchange membrane 10. The amount of the antibody solution added was 50 mL (concentration: 5.30 mg/mL), the flow rate was 1.5 mL/min, and the temperature was 25° C. After the flowing of the antibody solution, cation-exchange membrane 10 was washed with 10 mL of a 15 mmol/L tris buffer solution (pH 8) of 25° C. flowing at a flow rate of 1.5 mL/min. 60 mL of a solution was recovered by the flow-through step and the washing step. The recovered solution was applied to size exclusion chromatography (SEC). As a result, the content of the aggregate components was decreased. The results are shown in FIG. 3.

Example 18

In Example 18, cation-exchange membrane 10 and an antibody solution described below were used. The antibody solution used in Example 18 was a 15 mmol/L phosphate buffer solution (pH 7.0). The percentage of the aggregates (1) was 2.30%, the percentage of the aggregates (2) was 2.08%, and the percentage of the monomers was 95.62%.

The antibody solution containing aggregate components (impurities) and monomer components (physiologically active substance of interest) of the antibody proteins was contacted with cation-exchange membrane 10. The amount of the antibody solution added was 50 mL (concentration: 5.72 mg/mL), the flow rate was 1.5 mL/min, and the temperature was 25° C. After the flowing of the antibody solution, cation-exchange membrane 10 was washed with 10 mL of a 15 mmol/L phosphate buffer solution (pH 7.0) of 25° C. flowing at a flow rate of 1.5 mL/min. 60 mL of a solution was recovered by the flow-through step and the washing step. The recovered solution was applied to size exclusion chromatography (SEC). As a result, the content of the aggregate components was decreased. The results are shown in FIG. 3.

Example 19

In Example 19, cation-exchange membrane 12 described below was used. Cation-exchange membrane 12 was synthesized as follows: 2.57 g of 2-hydroxyethyl methacrylate, 1.29 g of ethylene glycol dimethacrylate, and 0.51 g of methacrylic acid were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 25 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 5.11 g of a cation-exchange membrane having a graft ratio of 70%. The cation-exchange group density measured in the same way as in Example 1 was 178 mmol/L. The resultant was made into a module (membrane volume: 0.25 mL) to prepare cation-exchange membrane 12 according to Example 19. The mass percentages of cation-exchange group-containing monomers and neutral monomers were 0.109 and 0.891, respectively.

The antibody solution used in Example 19 was a 15 mmol/L tris buffer solution (pH 7.0). The percentage of the aggregates (1) was 2.99%, the percentage of the aggregates (2) was 2.31%, and the percentage of the monomers was 94.70%.

The antibody solution containing aggregate components (impurities) and monomer components (physiologically active substance of interest) of the antibody proteins was contacted with cation-exchange membrane 12. The amount of the antibody solution added was 22 mL (concentration: 5.33 mg/mL), the flow rate was 1.5 mL/min, and the temperature was 25° C. After the flowing of the antibody solution, cation-exchange membrane 12 was washed with 10 mL of a 15 mmol/L tris buffer solution (pH 7.0) of 25° C. flowing at a flow rate of 1.5 mL/min. 32 mL of a solution was recovered by the flow-through step and the washing step. The recovered solution was applied to size exclusion chromatography (SEC). As a result, the content of the aggregate components was decreased. The results are shown in FIG. 3.

Example 20

In Example 20, cation-exchange membrane 13 described below was used. Cation-exchange membrane 13 was synthesized as follows: 2.69 g of 2-hydroxyethyl methacrylate, 1.17 g of ethylene glycol dimethacrylate, and 0.51 g of methacrylic acid were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 25 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 5.16 g of a cation-exchange membrane having a graft ratio of 70%. The cation-exchange group density measured in the same way as in Example 1 was 176 mmol/L. The resultant was made into a module (membrane volume: 0.25 mL) to prepare cation-exchange membrane 13 according to Example 20. The mass percentages of cation-exchange group-containing monomers and neutral monomers were 0.105 and 0.895, respectively.

The antibody solution used in Example 20 was a 15 mmol/L tris buffer solution (pH 7.0). The percentage of the aggregates (1) was 2.48%, the percentage of the aggregates (2) was 2.24%, and the percentage of the monomers was 95.29%.

The antibody solution containing aggregate components (impurities) and monomer components (physiologically active substance of interest) of the antibody proteins was contacted with cation-exchange membrane 13. The amount of the antibody solution added was 22 mL (concentration: 5.70 mg/mL), the flow rate was 1.5 mL/min, and the temperature was 25° C. After the flowing of the antibody solution, cation-exchange membrane 13 was washed with 10 mL of a 15 mmol/L tris buffer solution (pH 7.0) of 25° C. flowing at a flow rate of 1.5 mL/min. 32 mL of a solution was recovered by the flow-through step and the washing step. The recovered solution was applied to size exclusion chromatography (SEC). As a result, the content of the aggregate components was decreased. The results are shown in FIG. 3.

Example 21

In Example 21, cation-exchange membrane 14 described below was used. Cation-exchange membrane 14 was synthesized as follows: 2.50 g of 2-hydroxyethyl methacrylate, 1.36 g of diethylene glycol dimethacrylate, and 0.51 g of methacrylic acid were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 25 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 5.16 g of a cation-exchange membrane having a graft ratio of 70%. The cation-exchange group density measured in the same way as in Example 1 was 176 mmol/L. The resultant was made into a module (membrane volume: 0.25 mL) to prepare cation-exchange membrane 14 according to Example 21. The mass percentages of cation-exchange group-containing monomers and neutral monomers were 0.105 and 0.895, respectively.

The antibody solution used in Example 21 was a 15 mmol/L tris buffer solution (pH 7.0). The percentage of the aggregates (1) was 2.73%, the percentage of the aggregates (2) was 2.10%, and the percentage of the monomers was 95.16%.

The antibody solution containing aggregate components (impurities) and monomer components (physiologically active substance of interest) of the antibody proteins was contacted with cation-exchange membrane 14. The amount of the antibody solution added was 40 mL (concentration: 5.52 mg/mL), the flow rate was 1.5 mL/min, and the temperature was 25° C. After the flowing of the antibody solution, cation-exchange membrane 14 was washed with 10 mL of a 15 mmol/L tris buffer solution (pH 7.0) of 25° C. flowing at a flow rate of 1.5 mL/min. 50 mL of a solution was recovered by the flow-through step and the washing step. The recovered solution was applied to size exclusion chromatography (SEC). As a result, the content of the aggregate components was decreased. The results are shown in FIG. 3.

Example 22

In Example 22, cation-exchange membrane 15 described below was used. Cation-exchange membrane 15 was synthesized as follows: 3.08 g of 2-hydroxyethyl methacrylate, 1.54 g of butyl methacrylate, and 0.57 g of methacrylic acid were dissolved in 240 mL of an aqueous solution containing 50% by volume of t-butyl alcohol, and the solution was used as a reaction solution after nitrogen bubbling for 30 minutes. 5.80 g (15 cm, 30 filaments) of polyvinylidene fluoride porous hollow fiber having an outer diameter of 2.0 mm, an inner diameter of 1.1 mm, and an average pore size of 0.45 um was placed in a closed container, and the inside air of the container was replaced with nitrogen. Then, the container was cooled with dry ice from outside while irradiated with 25 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 8.36 g of a cation-exchange membrane having a graft ratio of 46%. The cation-exchange group density measured in the same way as in Example 1 was 227 mmol/L. The resultant was made into a module (membrane volume: 0.11 mL) to prepare cation-exchange membrane 15 according to Example 22. The mass percentages of cation-exchange group-containing monomers and neutral monomers were 0.115 and 0.885, respectively.

The antibody solution used in Example 22 was a 15 mmol/L tris buffer solution (pH 7.0). The percentage of the aggregates (1) was 3.14%, the percentage of the aggregates (2) was 2.03%, and the percentage of the monomers was 94.82%.

The antibody solution containing aggregate components (impurities) and monomer components (physiologically active substance of interest) of the antibody proteins was contacted with cation-exchange membrane 15. The amount of the antibody solution added was 10 mL (concentration: 5.53 mg/mL), the flow rate was 0.7 mL/min, and the temperature was 25° C. After the flowing of the antibody solution, cation-exchange membrane 15 was washed with 5 mL of a 15 mmol/L tris buffer solution (pH 7.0) of 25° C. flowing at a flow rate of 0.7 mL/min. 15 mL of a solution was recovered by the flow-through step and the washing step. The recovered solution was applied to size exclusion chromatography (SEC). As a result, the content of the aggregate components was decreased. The results are shown in FIG. 3.

Example 23

In Example 23, cation-exchange membrane 16 described below was used. Cation-exchange membrane 16 was synthesized as follows: 3.85 g of 2-hydroxyethyl methacrylate, 0.77 g of butyl methacrylate, and 0.57 g of methacrylic acid were dissolved in 240 mL of an aqueous solution containing 50% by volume of t-butyl alcohol, and the solution was used as a reaction solution after nitrogen bubbling for 30 minutes. 5.80 g (15 cm, 30 filaments) of polyvinylidene fluoride porous hollow fiber having an outer diameter of 2.0 mm, an inner diameter of 1.1 mm, and an average pore size of 0.45 um was placed in a closed container, and the inside air of the container was replaced with nitrogen. Then, the container was cooled with dry ice from outside while irradiated with 25 kGy of γ ray to generate radicals. The polyethylene porous hollow fiber having the obtained radicals was transferred to a glass container, and oxygen in the reaction tube was removed by decreasing the pressure to 200 Pa or lower.

140 mL of the reaction solution adjusted to 40° C. was introduced to the container, which was then left standing for 16 hours. Then, the hollow fiber was washed with methanol and dried in vacuum in a vacuum dryer to obtain 8.26 g of a cation-exchange membrane having a graft ratio of 44%. The cation-exchange group density measured in the same way as in Example 1 was 198 mmol/L. The resultant was made into a module (membrane volume: 0.11 mL) to prepare cation-exchange membrane 16 according to Example 23. The mass percentages of cation-exchange group-containing monomers and neutral monomers were 0.104 and 0.896, respectively.

The antibody solution used in Example 23 was a 15 mmol/L tris buffer solution (pH 7.0). The percentage of the aggregates (1) was 4.41%, the percentage of the aggregates (2) was 2.16%, and the percentage of the monomers was 93.43%.

The antibody solution containing aggregate components (impurities) and monomer components (physiologically active substance of interest) of the antibody proteins was contacted with cation-exchange membrane 16. The amount of the antibody solution added was 18 mL (concentration: 5.53 mg/mL), the flow rate was 0.7 mL/min, and the temperature was 25° C. After the flowing of the antibody solution, cation-exchange membrane 16 was washed with 5 mL of a 15 mmol/L tris buffer solution (pH 7.0) of 25° C. flowing at a flow rate of 0.7 mL/min. 23 mL of a solution was recovered by the flow-through step and the washing step. The recovered solution was applied to size exclusion chromatography (SEC). As a result, the content of the aggregate components was decreased. The results are shown in FIG. 3.

Example 24

In Example 24, cation-exchange membrane 17 described below was used. Cation-exchange membrane 17 was synthesized as follows: 4.62 g of 2-hydroxyethyl methacrylate, and 0.57 g of methacrylic acid were dissolved in 240 mL of an aqueous solution containing 50% by volume of t-butyl alcohol, and the solution was used as a reaction solution after nitrogen bubbling for 30 minutes. 5.80 g (15 cm, 30 filaments) of polyvinylidene fluoride porous hollow fiber having an outer diameter of 2.0 mm, an inner diameter of 1.1 mm, and an average pore size of 0.45 um was placed in a closed container, and the inside air of the container was replaced with nitrogen. Then, the container was cooled with dry ice from outside while irradiated with 25 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 7.99 g of a cation-exchange membrane having a graft ratio of 39%. The cation-exchange group density measured in the same way as in Example 1 was 214 mmol/L. The resultant was made into a module (membrane volume: 0.11 mL) to prepare cation-exchange membrane 17 according to Example 24. The mass percentages of cation-exchange group-containing monomers and neutral monomers were 0.126 and 0.874, respectively.

The antibody solution used in Example 24 was a 15 mmol/L tris buffer solution (pH 7.0). The percentage of the aggregates (1) was 2.42%, the percentage of the aggregates (2) was 1.77%, and the percentage of the monomers was 95.81%.

The antibody solution containing aggregate components (impurities) and monomer components (physiologically active substance of interest) of the antibody proteins was contacted with cation-exchange membrane 17. The amount of the antibody solution added was 18 mL (concentration: 5.64 mg/mL), the flow rate was 0.2 mL/min, and the temperature was 25° C. After the flowing of the antibody solution, cation-exchange membrane 17 was washed with 5 mL of a 15 mmol/L tris buffer solution (pH 7.0) of 25° C. flowing at a flow rate of 0.2 mL/min. 23 mL of a solution was recovered by the flow-through step and the washing step. The recovered solution was applied to size exclusion chromatography (SEC). As a result, the content of the aggregate components was decreased. The results are shown in FIG. 3.

Example 25

In Example 25, cation-exchange membrane 18 described below was used. Cation-exchange membrane 18 was synthesized as follows: 3.85 g of 2-hydroxyethyl methacrylate, 0.77 g of butyl methacrylate, and 0.57 g of methacrylic acid were dissolved in 240 mL of an aqueous solution containing 50% by volume of t-butyl alcohol, and the solution was used as a reaction solution after nitrogen bubbling for 30 minutes. 5.80 g (15 cm, 30 filaments) of polyvinylidene fluoride porous hollow fiber having an outer diameter of 2.0 mm, an inner diameter of 1.1 mm, and an average pore size of 0.65 um was placed in a closed container, and the inside air of the container was replaced with nitrogen. Then, the container was cooled with dry ice from outside while irradiated with 25 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 8.29 g of a cation-exchange membrane having a graft ratio of 43%. The cation-exchange group density measured in the same way as in Example 1 was 209 mmol/L. The resultant was made into a module (membrane volume: 0.11 mL) to prepare cation-exchange membrane 18 according to Example 25. The mass percentages of cation-exchange group-containing monomers and neutral monomers were 0.108 and 0.892, respectively.

The antibody solution used in Example 25 was a 15 mmol/L tris buffer solution (pH 7.0). The percentage of the aggregates (1) was 2.96%, the percentage of the aggregates (2) was 2.01%, and the percentage of the monomers was 95.03%.

The antibody solution containing aggregate components (impurities) and monomer components (physiologically active substance of interest) of the antibody proteins was contacted with cation-exchange membrane 18. The amount of the antibody solution added was 18 mL (concentration: 5.61 mg/mL), the flow rate was 0.7 mL/min, and the temperature was 25° C. After the flowing of the antibody solution, cation-exchange membrane 18 was washed with 5 mL of a 15 mmol/L tris buffer solution (pH 7.0) of 25° C. flowing at a flow rate of 0.7 mL/min. 23 mL of a solution was recovered by the flow-through step and the washing step. The recovered solution was applied to size exclusion chromatography (SEC). As a result, the content of the aggregate components was decreased. The results are shown in FIG. 3.

Example 26

In Example 26, cation-exchange membrane 19 described below was used. Cation-exchange membrane 19 was synthesized as follows: 4.62 g of 2-hydroxyethyl methacrylate, and 0.57 g of methacrylic acid were dissolved in 240 mL of an aqueous solution containing 50% by volume of t-butyl alcohol, and the solution was used as a reaction solution after nitrogen bubbling for 30 minutes. 5.80 g (15 cm, 30 filaments) of polyvinylidene fluoride porous hollow fiber having an outer diameter of 2.0 mm, an inner diameter of 1.1 mm, and an average pore size of 0.65 um was placed in a closed container, and the inside air of the container was replaced with nitrogen. Then, the container was cooled with dry ice from outside while irradiated with 25 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 8.17 g of a cation-exchange membrane having a graft ratio of 41%. The cation-exchange group density measured in the same way as in Example 1 was 223 mmol/L. The resultant was made into a module (membrane volume: 0.11 mL) to prepare cation-exchange membrane 19 according to Example 26. The mass percentages of cation-exchange group-containing monomers and neutral monomers were 0.127 and 0.873, respectively.

The antibody solution used in Example 26 was a 15 mmol/L tris buffer solution (pH 7.0). The percentage of the aggregates (1) was 2.83%, the percentage of the aggregates (2) was 1.96%, and the percentage of the monomers was 95.21%.

The antibody solution containing aggregate components (impurities) and monomer components (physiologically active substance of interest) of the antibody proteins was contacted with cation-exchange membrane 19. The amount of the antibody solution added was 18 mL (concentration: 5.69 mg/mL), the flow rate was 0.7 mL/min, and the temperature was 25° C. After the flowing of the antibody solution, cation-exchange membrane 19 was washed with 5 mL of a 15 mmol/L tris buffer solution (pH 7.0) of 25° C. flowing at a flow rate of 0.7 mL/min. 23 mL of a solution was recovered by the flow-through step and the washing step. The recovered solution was applied to size exclusion chromatography (SEC). As a result, the content of the aggregate components was decreased. The results are shown in FIG. 3.

Example 27

In Example 27, cation-exchange membrane 20 described below was used. Cation-exchange membrane 20 was synthesized as follows: 2.99 g of 2-hydroxyethyl methacrylate, 1.63 g of diethylene glycol dimethacrylate, and 0.57 g of methacrylic acid were dissolved in 240 mL of an aqueous solution containing 50% by volume of t-butyl alcohol, and the solution was used as a reaction solution after nitrogen bubbling for 30 minutes. 5.80 g (15 cm, 30 filaments) of polyvinylidene fluoride porous hollow fiber having an outer diameter of 2.0 mm, an inner diameter of 1.1 mm, and an average pore size of 0.65 um was placed in a closed container, and the inside air of the container was replaced with nitrogen. Then, the container was cooled with dry ice from outside while irradiated with 25 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 8.42 g of a cation-exchange membrane having a graft ratio of 45%. The cation-exchange group density measured in the same way as in Example 1 was 241 mmol/L. The resultant was made into a module (membrane volume: 0.11 mL) to prepare cation-exchange membrane 20 according to Example 27. The mass percentages of cation-exchange group-containing monomers and neutral monomers were 0.119 and 0.881, respectively.

The antibody solution used in Example 27 was a 15 mmol/L tris buffer solution (pH 7.0). The percentage of the aggregates (1) was 2.54%, the percentage of the aggregates (2) was 1.93%, and the percentage of the monomers was 95.53%.

The antibody solution containing aggregate components (impurities) and monomer components (physiologically active substance of interest) of the antibody proteins was contacted with cation-exchange membrane 20. The amount of the antibody solution added was 18 mL (concentration: 5.51 mg/mL), the flow rate was 0.7 mL/min, and the temperature was 25° C. After the flowing of the antibody solution, cation-exchange membrane 20 was washed with 5 mL of a 15 mmol/L tris buffer solution (pH 7.0) of 25° C. flowing at a flow rate of 0.7 mL/min. 23 mL of a solution was recovered by the flow-through step and the washing step. The recovered solution was applied to size exclusion chromatography (SEC). As a result, the content of the aggregate components was decreased. The results are shown in FIG. 3.

Example 28

In Example 28, cation-exchange membrane 21 described below was used. Cation-exchange membrane 21 was synthesized as follows: 3.09 g of N-isopropylacrylamide, 1.29 g of butyl methacrylate, 0.51 g of glycidyl methacrylate, and 0.26 g of t-butyl methacrylate were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 200 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 5.12 g of a cation-exchange membrane precursor having a graft ratio of 71%.

The hollow fiber containing the graft chain introduced by the radiation graft polymerization method was added to 200 g of a mixed aqueous solution of sodium sulfite and IPA (sodium sulfite/IPA/pure water=10/15/75 wt %) and reacted at 80° C. for 24 hours to convert the epoxy groups in the graft chain to sulfonic acid groups. The hollow fiber thus reacted was washed with pure water. Then, this hollow fiber was added into 0.5 mol/L sulfuric acid and reacted at 80° C. for 2 hours to convert the remaining epoxy groups in the graft chain to diol groups. Further, t-butyl groups were deprotected through reaction with 4 mL of methanesulfonic acid in 140 mL of chloroform and converted to carboxyl groups.

The membrane volume and the total cation-exchange group density were measured in the same way as in Example 1 and were consequently 1.0 mL and 49 mmol/L, respectively.

The sulfonic acid group density was determined by the following method: all sulfonic acid groups were hydrogenated by dipping in 1 mol/L hydrochloric acid for 1 hour. Hydrochloric acid was removed by washing with pure water, and then, hydrogen chloride was eluted by the addition of 10 mL of a 1 mol/L aqueous sodium chloride solution. The membrane was left for 1 hour, and then, the aqueous sodium chloride solution containing hydrogen chloride was recovered. 10 mL of a 1 mol/L aqueous sodium chloride solution was further added thereto. The membrane was left for 1 hour, and hydrogen chloride remaining in the membrane was recovered by recovering the solution. The recovered products were combined and titrated using a 0.01 mol/L aqueous sodium hydroxide solution. As a result, 2.09 mL was required for neutralization. The blank was 0.29 mL, revealing that sulfonic acid groups carried by the membrane were 18 umol. This value was divided by the membrane volume to confirm that the density was 18 mmol/L. The carboxyl group density can be determined by subtracting the sulfonic acid group density from the total cation-exchange group density and was 31 mmol/L. The resultant was made into a module (membrane volume: 0.25 mL) to prepare cation-exchange membrane 21 according to Example 28. The mass percentages of cation-exchange group-containing monomers and neutral monomers were 0.047 and 0.953, respectively.

The antibody solution used in Example 28 was a 15 mmol/L acetate buffer solution (pH 6.0). The percentage of the aggregates (1) was 2.80%, the percentage of the aggregates (2) was 3.21%, and the percentage of the monomers was 93.99%.

The antibody solution containing aggregate components (impurities) and monomer components (physiologically active substance of interest) of the antibody proteins was contacted with cation-exchange membrane 21. The amount of the antibody solution added was 20 mL (concentration: 4.99 mg/mL), the flow rate was 1.5 mL/min, and the temperature was 25° C. After the flowing of the antibody solution, cation-exchange membrane 21 was washed with 10 mL of a 15 mmol/L acetate buffer solution (pH 6.0) of 25° C. flowing at a flow rate of 1.5 mL/min. 30 mL of a solution was recovered by the flow-through step and the washing step. The recovered solution was applied to size exclusion chromatography (SEC). As a result, the content of the aggregate components was decreased. The results are shown in FIG. 3.

Example 29

In Example 29, cation-exchange membrane 21 and an antibody solution described below were used. The antibody solution used in Example 29 was a 15 mmol/L tris buffer solution (pH 7.0). The percentage of the aggregates (1) was 1.77%, the percentage of the aggregates (2) was 1.78%, and the percentage of the monomers was 96.44%.

The antibody solution containing aggregate components (impurities) and monomer components (physiologically active substance of interest) of the antibody proteins was contacted with cation-exchange membrane 21. The amount of the antibody solution added was 20 mL (concentration: 4.74 mg/mL), the flow rate was 1.5 mL/min, and the temperature was 25° C. After the flowing of the antibody solution, cation-exchange membrane 21 was washed with 10 mL of a 15 mmol/L tris buffer solution (pH 7.0) of 25° C. flowing at a flow rate of 1.5 mL/min. 30 mL of a solution was recovered by the flow-through step and the washing step. The recovered solution was applied to size exclusion chromatography (SEC). As a result, the content of the aggregate components was decreased. The results are shown in FIG. 3.

Comparative Example 1

In Comparative Example 1, cation-exchange membrane 22 described below was used which had a cation-exchange group density of smaller than 30 mmol/L. Cation-exchange membrane 22 was synthesized as follows: 3.09 g of N-isopropylacrylamide, 1.86 g of butyl methacrylate, and 0.2 g of methacrylic acid were dissolved in 240 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 200 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 5.22 g of a cation-exchange membrane having a graft ratio of 74%. The cation-exchange group density measured in the same way as in Example 1 was 27 mmol/L, which was lower than the density of 30 mmol/L. The mass percentages of cation-exchange group-containing monomers and neutral monomers were 0.017 and 0.983, respectively. The resultant was made into a module (membrane volume: 0.25 mL) to prepare cation-exchange membrane 22 according to Comparative Example 1.

The antibody solution used in Comparative Example 1 was a 15 mmol/L tris buffer solution (pH 7.0). The percentage of the aggregates (1) was 2.27%, the percentage of the aggregates (2) was 1.86%, and the percentage of the monomers was 95.87%.

The antibody solution containing aggregate components (impurities) and monomer components (physiologically active substance of interest) of the antibody proteins was contacted with cation-exchange membrane 22. The amount of the antibody solution added was 20 mL (concentration: 5.13 mg/mL), the flow rate was 1.5 mL/min, and the temperature was 25° C. After the flowing of the antibody solution, cation-exchange membrane 22 was washed with 10 mL of a 15 mmol/L tris buffer solution (pH 7.0) of 25° C.

flowing at a flow rate of 1.5 mL/min. 30 mL of a solution was recovered by the flow-through step and the washing step. The recovered solution was applied to size exclusion chromatography (SEC). As a result, the content of the aggregate components was decreased, but was larger than that in Example 1. The results are shown in FIG. 3.

Comparative Example 2

In Comparative Example 2, cation-exchange membrane 23 described below was used which had only strong cation-exchange groups having a cation-exchange group density of smaller than 30 mmol/L. Cation-exchange membrane 23 was synthesized as follows: 3.6 g of N-isopropylacrylamide, 1.8 g of butyl methacrylate, and 0.6 g of glycidyl methacrylate were dissolved in 280 mL of an aqueous solution containing 50% by volume of t-butyl alcohol, and the solution was used as a reaction solution after nitrogen bubbling for 30 minutes. 3.00 g (15 cm, 15 filaments) of polyethylene porous hollow fiber having an outer diameter of 3.0 mm, an inner diameter of 2.0 mm, and an average pore size of 0.25 um was placed in a closed container, and the inside air of the container was replaced with nitrogen. Then, the container was cooled with dry ice from outside while irradiated with 200 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 5.11 g of a cation-exchange membrane precursor having a graft ratio of 70%.

The hollow fiber containing the graft chain introduced by the radiation graft polymerization method was added to 200 g of a mixed aqueous solution of sodium sulfite and IPA (sodium sulfite/IPA/pure water=10/15/75 wt %) and reacted at 80° C. for 24 hours to convert the epoxy groups in the graft chain to sulfonic acid groups. The hollow fiber thus reacted was washed with pure water. Then, this hollow fiber was added into 0.5 mol/L sulfuric acid and reacted at 80° C. for 2 hours to convert the remaining epoxy groups in the graft chain to diol groups. The cation-exchange group density measured in the same way as in Example 1 was 18 mmol/L, which was lower than the density of 30 mmol/L. The mass percentages of cation-exchange group-containing monomers and neutral monomers were 0.03 and 0.97, respectively. The resultant was made into a module (membrane volume: 0.25 mL) to prepare cation-exchange membrane 23 according to Comparative Example 2.

The antibody solution used in Comparative Example 2 was a 15 mmol/L acetate buffer solution (pH 6.0). The percentage of the aggregates (1) was 2.03%, the percentage of the aggregates (2) was 2.06%, and the percentage of the monomers was 95.91%.

The antibody solution containing aggregate components (impurities) and monomer components (physiologically active substance of interest) of the antibody proteins was contacted with cation-exchange membrane 23. The amount of the antibody solution added was 50 mL (concentration: 4.80 mg/mL), the flow rate was 1.5 mL/min, and the temperature was 25° C. After the flowing of the antibody solution, cation-exchange membrane 23 was washed with 10 mL of a 15 mmol/L acetate buffer solution (pH 6.0) of 25° C. flowing at a flow rate of 1.5 mL/min. 60 mL of a solution was recovered by the flow-through step and the washing step. The recovered solution was applied to size exclusion chromatography (SEC). As a result, the content of the aggregate components was decreased, but was large as compared with Examples, and this aggregate removal performance is insufficient for a large processing volume. The results are shown in FIG. 3.

Comparative Example 3

In Comparative Example 3, cation-exchange membrane 24 described below was used in which homopolymers were immobilized on the surface of a membrane matrix. Cation-exchange membrane 24 was synthesized as follows: 0.51 g of methacrylic acid was dissolved in 240 mL of an aqueous solution containing 50% by volume of t-butyl alcohol, and the solution was used as a reaction solution after nitrogen bubbling for 30 minutes. 3.0 g (15 cm, 15 filaments) of polyvinylidene fluoride porous hollow fiber having an outer diameter of 2.0 mm, an inner diameter of 1.1 mm, and an average pore size of 0.65 um was placed in a closed container, and the inside air of the container was replaced with nitrogen. Then, the container was cooled with dry ice from outside while irradiated with 25 kGy of γ ray to generate radicals. The polyethylene porous hollow fiber having the obtained radicals was transferred to a glass container, and oxygen in the reaction tube was removed by decreasing the pressure to 200 Pa or lower. 140 mL of the reaction solution adjusted to 40° C. was introduced to the container, which was then left standing for 16 hours. Then, the hollow fiber was washed with methanol and dried in vacuum in a vacuum dryer to obtain 3.28 g of a cation-exchange membrane having a graft ratio of 9%. The cation-exchange group density measured in the same way as in Example 1 was 183 mmol/L. The resultant was made into a module (membrane volume: 0.25 mL) to prepare cation-exchange membrane 24 according to Comparative Example 3. The mass percentages of cation-exchange group-containing monomers and neutral monomers were 1.0 and 0, respectively.

The antibody solution used in Comparative Example 3 was a 15 mmol/L tris buffer solution (pH 7.0). The percentage of the aggregates (1) was 2.12%, the percentage of the aggregates (2) was 2.31%, and the percentage of the monomers was 95.57%.

The antibody solution containing aggregate components (impurities) and monomer components (physiologically active substance of interest) of the antibody proteins was contacted with cation-exchange membrane 24. The amount of the antibody solution added was 20 mL (concentration: 5.15 mg/mL), the flow rate was 1.5 mL/min, and the temperature was 25° C. After the flowing of the antibody solution, cation-exchange membrane 24 was washed with 10 mL of a 15 mmol/L tris buffer solution (pH 7.0) of 25° C. flowing at a flow rate of 1.5 mL/min. 30 mL of a solution was recovered by the flow-through step and the washing step. The recovered solution was applied to size exclusion chromatography (SEC). As a result, the content of the aggregate components was decreased, but was large as compared with other examples. The results are shown in FIG. 3.

Example 30

Example 30 shows an example in which impurities were reduced by flow-through purification with a cation-exchange chromatographic support followed by flow-through purification with an anion-exchange chromatographic support.

(Cation-Exchange Chromatography Step)

In Example 30, cation-exchange membrane 10 was used in the cation-exchange step. The antibody solution used in Example 30 was a 15 mmol/L tris buffer solution (pH 7.0). The percentage of the aggregates (1) was 1.05%, the percentage of the aggregates (2) was 1.13%, and the percentage of the monomers was 97.82%. The content of HCP was 350 ppm, and the content of protein A was 3 ppm.

HCP and protein A were quantified by UV measurement using CHINESE HAMSTER OVARY Host Cell Proteins-3rd Generation ELISA kit from *Cygnus* Technologies and PROTEIN A ELISA kit from Thchnologies, respectively.

The antibody solution containing aggregate components (impurities) and monomer components (physiologically active substance of interest) of the antibody proteins, HCP, and protein A was contacted with cation-exchange membrane 10. The amount of the antibody solution added was 50 mL (concentration: 5.45 mg/mL), the flow rate was 1.5 mL/min, and the temperature was 25° C. After the flowing of the antibody solution, cation-exchange membrane 10 was washed with 10 mL of a 15 mmol/L tris buffer solution (pH 7.0) of 25° C. flowing at a flow rate of 1.5 mL/min. 60 mL of a solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 4.

(Anion-Exchange Chromatography Step)

In Example 30, Capto Q (GE Healthcare Biosciences Corp.) having a volume of 1 mL was used in the anion-exchange step. The antibody solution recovered by the cation-exchange step was adjusted to pH 7.8 by the addition of a 1 mol/L tris buffer solution and contacted with Capto Q. The amount of the antibody solution added was 50 mL (concentration: 4.01 mg/mL), the flow rate was 1.0 mL/min, and the temperature was 25° C. After the flowing of the antibody solution, Capto Q was washed with 5 mL of a 15 mmol/L tris buffer solution (pH 7.8) of 25° C. flowing at a flow rate of 1.0 mL/min. 55 mL of an antibody solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 4.

Example 31

Example 31 shows an example in which impurities were reduced by flow-through purification with an anion-exchange chromatographic support followed by flow-through purification with a cation-exchange chromatographic support.

(Anion-Exchange Chromatography Step)

In Example 31, Capto Q (GE Healthcare Biosciences Corp.) having a volume of 1 mL was used in the anion-exchange step. The antibody solution was a 15 mmol/L tris buffer solution (pH 7.8). The percentage of the aggregates (1) was 0.42%, the percentage of the aggregates (2) was 1.14%, and the percentage of the monomers was 98.44%. The content of HCP was 306 ppm, and the content of protein A was 3 ppm.

The antibody solution containing aggregate components (impurities) and monomer components (physiologically active substance of interest) of the antibody proteins, HCP, and protein A was contacted with Capto Q having a volume of 1 mL. The amount of the antibody solution added was 50 mL (concentration: 6.28 mg/mL), the flow rate was 1.0 mL/min, and the temperature was 25° C. After the flowing of the antibody solution, Capto Q was washed with 5 mL of a 15 mmol/L tris buffer solution (pH 7.8) of 25° C. flowing at a flow rate of 1.0 mL/min. 55 mL of a solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 4.

(Cation-Exchange Chromatography Step)

In Example 31, cation-exchange membrane 10 was used in the cation-exchange step. The antibody solution recovered by the anion-exchange step was adjusted to pH 7 by the addition of 0.1 mol/L hydrochloric acid and contacted with cation-exchange membrane 10. The amount of the antibody solution added was 50 mL (concentration: 4.65 mg/mL), the flow rate was 1.5 mL/min, and the temperature was 25° C. After the flowing of the antibody solution, cation-exchange membrane 10 was washed with 10 mL of a 15 mmol/L tris buffer solution (pH 7) of 25° C. flowing at a flow rate of 1.5 mL/min. 60 mL of an antibody solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 4.

Example 32

Example 32 shows an example in which impurities were reduced by purification with a cation-exchange chromatographic support followed by flow-through purification with an anion-exchange chromatographic support.

(Cation-Exchange Chromatography Step)

In Example 32, cation-exchange membrane 10 was used in the cation-exchange step. The antibody solution was a 15 mmol/L tris buffer solution (pH 7.0). The percentage of the aggregates (1) was 0.91%, the percentage of the aggregates (2) was 1.32%, and the percentage of the monomers was 97.77%. The content of HCP was 390 ppm, and the content of protein A was 3 ppm.

The antibody solution containing aggregate components (impurities) and monomer components (physiologically active substance of interest) of the antibody proteins, HCP, and protein A was contacted with cation-exchange membrane 10. The amount of the antibody solution added was 50 mL (concentration: 5.33 mg/mL), the flow rate was 1.5 mL/min, and the temperature was 25° C. After the flowing of the antibody solution, cation-exchange membrane 10 was washed with 10 mL of a 15 mmol/L tris buffer solution (pH 7.0) of 25° C. flowing at a flow rate of 1.5 mL/min. 60 mL of a solution was recovered by the flow-through step and the washing step. The same operation as above was further repeated five times. The recovered solution was analyzed by size exclusion chromatography (SEC) and ELISA. As a result, the contents of the aggregate components, HCP, and protein A were decreased. The results are shown in FIG. 4.

(Anion-Exchange Chromatography Step)

In Example 32, 0.25 mL of QyuSpeed D (Asahi Kasei Medical Co., Ltd.) was used in the anion-exchange step. The antibody solution recovered by the cation-exchange step was adjusted to pH 7.8 by the addition of a 1 mol/L tris buffer solution and contacted with QyuSpeed D. The amount of the antibody solution added was 310 mL (concentration: 3.80 mg/mL), the flow rate was 1.5 mL/min, and the temperature was 25° C. After the flowing of the antibody solution, QyuSpeed D was washed with 10 mL of a 15 mmol/L tris buffer solution (pH 7.8) flowing at a flow rate of 1.5 mL. 320 mL of an antibody solution was recovered by the flow-through step and the washing step. The recovered solution was analyzed by size exclusion chromatography (pHSEC) and ELISA. As a result, the contents of the aggregate components, HCP, and protein A were decreased. The results are shown in FIG. 4.

Example 33

In Example 33, a culture supernatant containing 0.163 g/L AE6F4 antibodies (human monoclonal antibodies) as antibody proteins was used, and a series of purification steps involving affinity chromatography, cation-exchange chromatography, and anion-exchange chromatography were performed without buffer replacement.

(Affinity Chromatography Step)

The operation of the affinity chromatography step according to Example 33 was performed at a flow rate of 4 mL/min (300 cm/hr). First, a column packed with 16 mL of Mabselect Sure was equilibrated with 80 mL of a phosphate buffer solution (20 mmol/L sodium phosphate+150 mmol/L NaCl (pH 8.0)), and 2.5 L of the culture supernatant containing the antibodies was added thereto so that the antibodies were adsorbed onto the column. Next, the column was washed by passing 80 mL of a phosphate buffer solution (20 mmol/L sodium phosphate+150 mmol/L NaCl (pH 8.0)) and further passing 48 mL of a tris/acetate buffer solution (100 mmol/L (pH 8.0)). Then, the antibodies were eluted from the column by passing 80 mL of a 25 mmol/L acetate buffer solution (pH 3.4) as an eluting solution. The eluate was adjusted to pH 7.0 by the addition of a 1 mol/L tris buffer solution to obtain an antibody solution. The obtained antibody solution had an electric conductivity of 1.7 mS/cm. The obtained antibody solution was mixed with an antibody solution having the same solution composition thereas and containing more aggregates to prepare an antibody solution for use in the cation-exchange chromatography step mentioned later. In the antibody solution, the percentage of the aggregates (1) was 0.72%, the percentage of the aggregates (2) was 1.04%, and the percentage of the monomers was 98.24%. The content of HCP was 298 ppm, and the content of protein A was 3 ppm.

(Cation-Exchange Chromatography Step)

Cation-exchange membrane 10 was used in the cation-exchange chromatography step according to Example 33. The amount of the antibody solution added to cation-exchange membrane 10 was 82 mL (concentration: 3.67 mg/mL), the flow rate was 1.5 mL/min, and the temperature was 25° C. After the flowing of the antibody solution in cation-exchange membrane 10, cation-exchange membrane 10 was washed by passing 10 mL of a buffer (pH 7.0) having the same composition as that for the antibody solution at a flow rate of 1.5 mL/min. 92 mL of a solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 5.

(Anion-Exchange Chromatography Step)

Capto Q (GE Healthcare Biosciences Corp.) having a volume of 1 mL was used in the anion-exchange step according to Example 33. The antibody solution recovered by the cation-exchange step was adjusted to pH 7.8 by the addition of a 1 mol/L tris buffer solution. The resulting antibody solution had an electric conductivity of 1.8 mS/cm. Then, the antibody solution was contacted with Capto Q. The amount of the antibody solution added to Capto Q was 82 mL (concentration: 2.96 mg/mL), the flow rate was 1.0 mL/min, and the temperature was 25° C. After the flowing of the antibody solution in Capto Q, Capto Q was washed by passing 5 mL of a buffer (pH 7.8) having the same composition as that for the antibody solution at a flow rate of 1.0 mL/min. A total of 87 mL of a solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 5.

Example 34

In Example 34, a culture supernatant containing 0.163 g/L AE6F4 antibodies (human monoclonal antibodies) as antibody proteins was used, and a series of purification steps involving affinity chromatography, anion-exchange chromatography, and cation-exchange chromatography were performed without buffer replacement.

(Affinity Chromatography Step)

The operation of the affinity chromatography step according to Example 34 was performed at a flow rate of 4 mL/min (300 cm/hr). First, a column packed with 16 mL of Mabselect Sure was equilibrated with 80 mL of a phosphate buffer solution (20 mmol/L sodium phosphate+150 mmol/L NaCl (pH 8.0)), and 2.5 L of the culture supernatant containing the antibodies was added thereto so that the antibodies were adsorbed onto the column. Next, the column was washed by passing 80 mL of a phosphate buffer solution (20 mmol/L sodium phosphate+150 mmol/L NaCl (pH 8.0)) and further passing 48 mL of a tris/acetate buffer solution (100 mmol/L (pH 8.0)). Then, the antibodies were eluted from the column by passing 80 mL of a 25 mmol/L acetate buffer solution (pH 3.4) as an eluting solution. The eluate was adjusted to pH 7.8 by the addition of a 1 mol/L tris buffer solution to obtain an antibody solution. The obtained antibody solution had an electric conductivity of 1.8 mS/cm. The obtained antibody solution was mixed with an antibody solution having the same solution composition thereas and containing more aggregates to prepare an antibody solution for use in the anion-exchange chromatography step mentioned later. In the antibody solution, the percentage of the aggregates (1) was 0.83%, the percentage of the aggregates (2) was 1.12%, and the percentage of the monomers was 98.05%. The content of HCP was 317 ppm, and the content of protein A was 3 ppm.

(Anion-Exchange Chromatography Step)

The antibody solution was purified in the anion-exchange step according to Example 34 using Capto Q (GE Healthcare Biosciences Corp.) having a volume of 1 mL. The amount of the antibody solution added to Capto Q was 81 mL (concentration: 3.72 mg/mL), the flow rate was 1.0 mL/min, and the temperature was 25° C. After the flowing of the antibody solution in Capto Q, Capto Q was washed by passing 5 mL of a buffer (pH 7.8) having the same composition as that for the antibody solution at a flow rate of 1.0 mL/min. A total of 86 mL of a solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 5.

(Cation-Exchange Chromatography Step)

Cation-exchange membrane 10 was used in the cation-exchange chromatography step according to Example 34. The antibody solution recovered by the anion-exchange step was adjusted to pH 7.0 by the addition of acetic acid. The resulting antibody solution had an electric conductivity of 1.9 mS/cm. Then, the antibody solution was contacted with cation-exchange membrane 10. The amount of the antibody solution added was 80 mL (concentration: 3.33 mg/mL), the flow rate was 1.5 mL/min, and the temperature was 25° C. After the flowing of the antibody solution in cation-exchange membrane 10, cation-exchange membrane 10 was washed by passing 10 mL of a buffer (pH 7.0) having the same composition as that for the antibody solution at a flow rate of 1.5 mL/min. A total of 90 mL of a solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 5.

Example 35

In Example 35, a culture supernatant containing 0.163 g/L AE6F4 antibodies (human monoclonal antibodies) as antibody proteins was used, and a series of purification steps involving affinity chromatography, cation-exchange chromatography, and anion-exchange chromatography were performed without buffer replacement.

(Affinity Chromatography Step)

The operation of the affinity chromatography step according to Example 35 was performed at a flow rate of 4 mL/min (300 cm/hr). First, a column packed with 16 mL of Mabselect Sure was equilibrated with 80 mL of a phosphate buffer solution (20 mmol/L sodium phosphate+150 mmol/L NaCl (pH 8.0)), and 2.5 L of the culture supernatant containing the antibodies was added thereto so that the antibodies were adsorbed onto the column. Next, the column was washed by passing 80 mL of a phosphate buffer solution (20 mmol/L sodium phosphate+150 mmol/L NaCl (pH 8.0)) and further passing 48 mL of a tris/acetate buffer solution (100 mmol/L (pH 8.0)). Then, the antibodies were eluted from the column by passing 80 mL of a 25 mmol/L acetate buffer solution (pH 3.4) as an eluting solution. The eluate was adjusted to pH 7.0 by the addition of a 1 mol/L tris buffer solution to obtain an antibody solution. The obtained antibody solution had an electric conductivity of 1.7 mS/cm. The obtained antibody solution was mixed with an antibody solution having the same solution composition thereas and containing more aggregates to prepare an antibody solution for use in the cation-exchange chromatography step mentioned later. In the antibody solution, the percentage of the aggregates (1) was 0.79%, the percentage of the aggregates (2) was 1.16%, and the percentage of the monomers was 98.05%. The content of HCP was 390 ppm, and the content of protein A was 3 ppm.

(Cation-Exchange Chromatography Step)

Cation-exchange membrane 10 was used in the cation-exchange chromatography step according to Example 35. The amount of the antibody solution added was 82 mL (concentration: 3.71 mg/mL), the flow rate was 1.5 mL/min, and the temperature was 25° C. After the flowing of the antibody solution in cation-exchange membrane 10, cation-exchange membrane 10 was washed by passing 10 mL of a buffer (pH 7.0) having the same composition as that for the antibody solution at a flow rate of 1.5 mL/min. A total of 92 mL of a solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 5.

(Anion-Exchange Chromatography Step)

QyuSpeed D(Asahi Kasei Medical Co., Ltd.) having a volume of 0.25 mL was used in the anion-exchange step according to Example 35. The antibody solution recovered by the cation-exchange step was adjusted to pH 7.8 by the addition of a 1 mol/L tris buffer solution. The resulting antibody solution had an electric conductivity of 1.8 mS/cm. Then, the antibody solution was contacted with QyuSpeed D. The amount of the antibody solution added to QyuSpeed D was 82 mL (concentration: 2.99 mg/mL), the flow rate was 1.5 mL/min, and the temperature was 25° C. After the flowing of the antibody solution in QyuSpeed D, QyuSpeed D was washed by passing 10 mL of a buffer (pH 7.8) having the same composition as that for the antibody solution at a flow rate of 1.5 mL/min. A total of 92 mL of a solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 5.

Example 36

In Example 36, a culture supernatant containing 0.163 g/L AE6F4 antibodies (human monoclonal antibodies) as antibody proteins was used, and a series of purification steps involving affinity chromatography, anion-exchange chromatography, and cation-exchange chromatography were performed without buffer replacement.

(Affinity Chromatography Step)

The operation of the affinity chromatography step according to Example 36 was performed at a flow rate of 4 mL/min (300 cm/hr). First, a column packed with 16 mL of Mabselect Sure was equilibrated with 80 mL of a phosphate buffer solution (20 mmol/L sodium phosphate+150 mmol/L NaCl (pH 8.0)), and 2.5 L of the culture supernatant containing the antibodies was added thereto so that the antibodies were adsorbed onto the column. Next, the column was washed by passing 80 mL of a phosphate buffer solution (20 mmol/L sodium phosphate+150 mmol/L NaCl (pH 8.0)) and further passing 48 mL of a tris/acetate buffer solution (100 mmol/L (pH 8.0)). Then, the antibodies were eluted from the column by passing 80 mL of a 25 mmol/L acetate buffer solution (pH 3.4) as an eluting solution. The eluate was adjusted to pH 7.8 by the addition of a 1 mol/L tris buffer solution to obtain an antibody solution. The electric conductivity of the obtained antibody solution was 1.8 mS/cm. The obtained antibody solution was mixed with an antibody solution having the same solution composition thereas and containing more aggregates to prepare an antibody solution for use in the anion-exchange chromatography step mentioned later. In the antibody solution, the percentage of the aggregates (1) was 0.78%, the percentage of the aggregates (2) was 1.21%, and the percentage of the monomers was 98.01%. The content of HCP was 365 ppm, and the content of protein A was 3 ppm.

(Anion-Exchange Chromatography Step)

QyuSpeed D (Asahi Kasei Medical Co., Ltd.) having a volume of 0.25 mL was used in the anion-exchange step according to Example 36. The amount of the antibody solution added to QyuSpeed D was 80 mL (concentration: 3.69 mg/mL), the flow rate was 1.5 mL/min, and the temperature was 25° C. After the flowing of the antibody solution in QyuSpeed D, QyuSpeed D was washed by passing 10 mL of a buffer (pH 7.8) having the same composition as that for the antibody solution at a flow rate of 1.5 mL/min. A total of 90 mL of a solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 5.

(Cation-Exchange Chromatography Step)

Cation-exchange membrane 10 was used in the cation-exchange chromatography step according to Example 36. The antibody solution recovered by the anion-exchange step was adjusted to pH 7.0 by the addition of acetic acid. The resulting antibody solution had an electric conductivity of 1.9 mS/cm. Then, the antibody solution was contacted with cation-exchange membrane 10. The amount of the antibody solution added was 80 mL (concentration: 3.17 mg/mL), the flow rate was 1.5 mL/min, and the temperature was 25° C. After the flowing of the antibody solution, cation-exchange membrane 10 was washed by passing 10 mL of a buffer (pH 7.0) having the same composition as that for the antibody solution at a flow rate of 1.5 mL/min. A total of 90 mL of a solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 5.

Example 37

In Example 37, a culture supernatant containing 0.163 g/L AE6F4 antibodies (human monoclonal antibodies) as antibody proteins was used, and a series of purification steps involving affinity chromatography, cation-exchange chromatography, and anion-exchange chromatography were performed without buffer replacement. In the anion-exchange chromatography step, the antibodies were loaded in an amount of 4 g or larger per volume of the support.

(Affinity Chromatography Step)

The operation of the affinity chromatography step according to Example 37 was performed at a flow rate of 20 mL/min (230 cm/hr). First, a column packed with 58 mL of Mabselect Sure was equilibrated with 300 mL of a phosphate buffer solution (20 mmol/L sodium phosphate+150 mmol/L NaCl (pH 8.0)), and 7 L of the culture supernatant containing the antibodies was added thereto so that the antibodies were adsorbed onto the column. Next, the column was washed by passing 300 mL of a phosphate buffer solution (20 mmol/L sodium phosphate+150 mmol/L NaCl (pH 8.0)) and further passing 180 mL of a tris/acetate buffer solution (100 mmol/L (pH 8.0)). Then, the antibodies were eluted from the column by passing 360 mL of a 25 mmol/L acetate buffer solution (pH 3.4) as an eluting solution. The eluate was adjusted to pH 7.0 by the addition of a 1 mol/L tris buffer solution to obtain an antibody solution. The obtained antibody solution had an electric conductivity of 1.7 mS/cm. The same operation as above was performed a total of twice, and the respective eluates were combined. The obtained antibody solution was mixed with an antibody solution having the same solution composition thereas and containing more aggregates to prepare an antibody solution for use in the cation-exchange chromatography step mentioned later. In the antibody solution, the percentage of the aggregates (1) was 0.56%, the percentage of the aggregates (2) was 1.79%, and the percentage of the monomers was 97.65%. The content of HCP was 349 ppm, and the content of protein A was 4 ppm.

(Cation-Exchange Chromatography Step)

Cation-exchange membrane 10 was used in the cation-exchange chromatography step according to Example 37. The amount of the antibody solution added was 100 mL (concentration: 2.60 mg/mL), the flow rate was 1.5 mL/min, and the temperature was 25° C. After the flowing of the antibody solution in cation-exchange membrane 10, cation-exchange membrane 10 was washed by passing 10 mL of a buffer (pH 7.0) having the same composition as that for the antibody solution at a flow rate of 1.5 mL/min. A total of 110 mL of a solution was recovered by the flow-through step and the washing step. The same operation as above was performed a total of five times. The recovered solutions were combined and analyzed by size exclusion chromatography (SEC) and ELISA. As a result, the contents of the aggregate components, HCP, and protein A were decreased. The results are shown in FIG. 5.

(Anion-Exchange Chromatography Step)

QyuSpeed D (Asahi Kasei Medical Co., Ltd.) having a volume of 0.25 mL was used in the anion-exchange step according to Example 37. The antibody solution recovered by the cation-exchange step was adjusted to pH 7.8 by the addition of a 1 mol/L tris buffer solution. The resulting antibody solution had an electric conductivity of 1.8 mS/cm. Then, the antibody solution was contacted with QyuSpeed D. The amount of the antibody solution added to QyuSpeed D was 500 mL (concentration: 2.08 mg/mL), the flow rate was 1.5 mL/min, and the temperature was 25° C. After the flowing of the antibody solution in QyuSpeed D, QyuSpeed D was washed by passing 10 mL of a buffer (pH 7.8) having the same composition as that for the antibody solution at a flow rate of 1.5 mL/min. A total of 510 mL of a solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 5.

Example 38

In Example 38, a culture supernatant containing 0.163 g/L AE6F4 antibodies (human monoclonal antibodies) as antibody proteins was used, and a series of purification steps involving affinity chromatography, cation-exchange chromatography, and anion-exchange chromatography were performed without buffer replacement. The operation of pH adjustment was not performed between the cation-exchange step and the anion-exchange step.

(Affinity Chromatography Step)

The operation of the affinity chromatography step according to Example 38 was performed at a flow rate of 20 mL/min (230 cm/hr). First, a column packed with 58 mL of Mabselect Sure was equilibrated with 300 mL of a phosphate buffer solution (20 mmol/L sodium phosphate+150 mmol/L NaCl (pH 8.0)), and 7 L of the culture supernatant containing the antibodies was added thereto so that the antibodies were adsorbed onto the column. Next, the column was washed by passing 300 mL of a phosphate buffer solution (20 mmol/L sodium phosphate+150 mmol/L NaCl (pH 8.0)) and further passing 180 mL of a tris/acetate buffer solution (100 mmol/L (pH 8.0)). Then, the antibodies were eluted from the column by passing 360 mL of a 25 mmol/L acetate buffer solution (pH 3.4) as an eluting solution. The eluate was adjusted to pH 7.0 by the addition of a 1 mol/L tris buffer solution to obtain an antibody solution. The obtained antibody solution had an electric conductivity of 1.7 mS/cm. The same operation as above was performed a total of twice, and the respective eluates were combined. The obtained antibody solution was mixed with an antibody solution having the same solution composition thereas and containing more aggregates to prepare an antibody solution for use in the cation-exchange chromatography step mentioned later. In the antibody solution, the percentage of the aggregates (1) was 0.99%, the percentage of the aggregates (2) was 0.98%, and the percentage of the monomers was 98.03%. The content of HCP was 306 ppm, and the content of protein A was 2 ppm.

(Cation-Exchange Chromatography Step)

Cation-exchange membrane 10 was used in the cation-exchange chromatography step according to Example 38. The amount of the antibody solution added was 120 mL (concentration: 2.40 mg/mL), the flow rate was 1.5 mL/min, and the temperature was 25° C. After the flowing of the antibody solution in cation-exchange membrane 10, cation-exchange membrane 10 was washed by passing 10 mL of a buffer (pH 7.0) having the same composition as that for the antibody solution at a flow rate of 1.5 mL/min. A total of 130 mL of a solution was recovered by the flow-through step and the washing step. The same operation as above was performed a total of five times. The recovered solutions were combined and analyzed by size exclusion chromatography (SEC) and ELISA. As a result, the contents of the aggregate components, HCP, and protein A were decreased. The results are shown in FIG. 5.

(Anion-Exchange Chromatography Step)

QyuSpeed D (Asahi Kasei Medical Co., Ltd.) having a volume of 0.25 mL was used in the anion-exchange step according to Example 38. The antibody solution recovered by the cation-exchange step was contacted with QyuSpeed D. The amount of the antibody solution added to QyuSpeed D was 480 mL (concentration: 1.95 mg/mL), the flow rate was 1.5 mL/min, and the temperature was 25° C. After the flowing of the antibody solution in QyuSpeed D, QyuSpeed D was washed by passing 10 mL of a buffer (pH 7.0) having the same composition as that for the antibody solution at a flow rate of 1.5 mL/min. A total of 490 mL of a solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 5.

Example 39

In Example 39, a culture supernatant containing 0.163 g/L AE6F4 antibodies (human monoclonal antibodies) as antibody proteins was used, and a series of purification steps involving affinity chromatography, cation-exchange chromatography, and anion-exchange chromatography were performed without buffer replacement. The operation of pH adjustment was not performed between the cation-exchange step and the anion-exchange step.

(Affinity Chromatography Step)

The operation of the affinity chromatography step according to Example 39 was performed at a flow rate of 20 mL/min (230 cm/hr). First, a column packed with 58 mL of Mabselect Sure was equilibrated with 300 mL of a phosphate buffer solution (20 mmol/L sodium phosphate+150 mmol/L NaCl (pH 8.0)), and 7 L of the culture supernatant containing the antibodies was added thereto so that the antibodies were adsorbed onto the column. Next, the column was washed by passing 300 mL of a phosphate buffer solution (20 mmol/L sodium phosphate+150 mmol/L NaCl (pH 8.0)) and further passing 180 mL of a tris/acetate buffer solution (100 mmol/L (pH 8.0)). Then, the antibodies were eluted from the column by passing 360 mL of a 25 mmol/L acetate buffer solution (pH 3.4) as an eluting solution. A portion of the eluate was adjusted to pH 7.5 by the addition of a 1 mol/L tris buffer solution to obtain an antibody solution. The obtained antibody solution had an electric conductivity of 2.2 mS/cm. The obtained antibody solution was mixed with an antibody solution having the same solution composition thereas and containing more aggregates to prepare an antibody solution for use in the cation-exchange chromatography step mentioned later. In the antibody solution, the percentage of the aggregates (1) was 0.50%, the percentage of the aggregates (2) was 0.91%, and the percentage of the monomers was 98.59%. The content of HCP was 443 ppm, and the content of protein A was 1 ppm.

(Cation-Exchange Chromatography Step)

Cation-exchange membrane 10 was used in the cation-exchange chromatography step according to Example 39. The amount of the antibody solution added was 130 mL (concentration: 2.08 mg/mL), the flow rate was 1.5 mL/min, and the temperature was 25° C. After the flowing of the antibody solution in cation-exchange membrane 10, cation-exchange membrane 10 was washed by passing 10 mL of a buffer (pH 7.5) having the same composition as that for the antibody solution at a flow rate of 1.5 mL/min. A total of 140 mL of a solution was recovered by the flow-through step and the washing step. The obtained antibody solution was analyzed by size exclusion chromatography (SEC) and ELISA. As a result, the contents of the aggregate components, HCP, and protein A were decreased. The results are shown in FIG. 5.

(Anion-Exchange Chromatography Step)

QyuSpeed D (Asahi Kasei Medical Co., Ltd.) having a volume of 0.25 mL was used in the anion-exchange step according to Example 39. The antibody solution recovered by the cation-exchange step was contacted with QyuSpeed D. The amount of the antibody solution added to QyuSpeed D was 125 mL (concentration: 1.79 mg/mL), the flow rate was 1.5 mL/min, and the temperature was 25° C. After the flowing of the antibody solution in QyuSpeed D, QyuSpeed D was washed by passing 10 mL of a buffer (pH 7.5) having the same composition as that for the antibody solution at a flow rate of 1.5 mL/min. A total of 135 mL of a solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 5.

Example 40

In Example 40, a culture supernatant containing 0.163 g/L AE6F4 antibodies (human monoclonal antibodies) as antibody proteins was used, and a series of purification steps involving affinity chromatography, cation-exchange chromatography, and anion-exchange chromatography were performed without buffer replacement. The operation of pH adjustment was not performed between the cation-exchange step and the anion-exchange step.

(Affinity Chromatography Step)

In Example 40, a portion of the eluate obtained by the affinity chromatography step of Example 39 was adjusted to pH 8.0 by the addition of a 1 mol/L tris buffer solution to obtain an antibody solution. The obtained antibody solution had an electric conductivity of 2.3 mS/cm. The obtained antibody solution was mixed with an antibody solution having the same solution composition thereas and containing more aggregates to prepare an antibody solution for use in the cation-exchange chromatography step mentioned later. In the antibody solution, the percentage of the aggregates (1) was 0.64%, the percentage of the aggregates (2)

was 1.08%, and the percentage of the monomers was 98.28%. The content of HCP was 588 ppm, and the content of protein A was 2 ppm.

(Cation-Exchange Chromatography Step)

Cation-exchange membrane 10 was used in the cation-exchange chromatography step according to Example 40. The amount of the antibody solution added was 130 mL (concentration: 2.05 mg/mL), the flow rate was 1.5 mL/min, and the temperature was 25° C. After the flowing of the antibody solution in cation-exchange membrane 10, cation-exchange membrane 10 was washed by passing 10 mL of a buffer (pH 8.0) having the same composition as that for the antibody solution at a flow rate of 1.5 mL/min. A total of 140 mL of a solution was recovered by the flow-through step and the washing step. The obtained antibody solution was analyzed by size exclusion chromatography (SEC) and ELISA. As a result, the contents of the aggregate components, HCP, and protein A were decreased. The results are shown in FIG. 5.

(Anion-Exchange Chromatography Step)

QyuSpeed D (Asahi Kasei Medical Co., Ltd.) having a volume of 0.25 mL was used in the anion-exchange step according to Example 40. The antibody solution recovered by the cation-exchange step was contacted with QyuSpeed D. The amount of the antibody solution added to QyuSpeed D was 125 mL (concentration: 1.75 mg/mL), the flow rate was 1.5 mL/min, and the temperature was 25° C. After the flowing of the antibody solution in QyuSpeed D, QyuSpeed D was washed by passing 10 mL of a buffer (pH 8.0) having the same composition as that for the antibody solution at a flow rate of 1.5 mL/min. A total of 135 mL of a solution was recovered by the flow-through step and the washing step. The recovered solution was analyzed by size exclusion chromatography (SEC) and ELISA. As a result, the contents of the aggregate components, HCP, and protein A were decreased. The results are shown in FIG. 5.

The invention claimed is:

1. A cation-exchange chromatographic support, comprising a membrane matrix and a copolymer immobilized on the surface of the membrane matrix, wherein the copolymer comprises a (meth)acrylamide-based compound and/or a (meth)acrylate-based compound as monomer units, and the support has one or more species of cation-exchange groups including at least a weak cation-exchange group at a density higher than 30 mmol/L per volume of the support.

2. The cation-exchange chromatographic support according to claim 1, wherein monomer units other than monomer units having the cation-exchange groups in the copolymer are neutral monomers having no charge, and the neutral monomers are a hydrophobic monomer unit and/or a hydrophilic monomer unit.

3. The cation-exchange chromatographic support according to claim 1, wherein the copolymer comprises at least one species of hydrophobic monomer unit as a monomer unit.

4. The cation-exchange chromatographic support according to claim 1, wherein the weak cation-exchange group is derived from any of an acrylic acid monomer, a methacrylic acid monomer, an acrylic acid compound monomer, and a methacrylic acid compound monomer.

5. The cation-exchange chromatographic support according to claim 1, wherein the weak cation-exchange group is derived from a methacrylic acid monomer.

6. The cation-exchange chromatographic support according to claim 2, wherein the mass percentage of the hydrophobic monomer unit and/or the hydrophilic monomer unit in the copolymer is higher than that of the cation-exchange group-containing monomer units.

7. The cation-exchange chromatographic support according to claim 1, wherein the one or more species of cation-exchange groups consist only of weak cation exchange groups.

8. The cation-exchange chromatographic support according to claim 1, wherein the one or more species of cation-exchange groups are a mixture of a weak cation-exchange group and a strong cation-exchange group.

9. The cation-exchange chromatographic support according to claim 1, wherein the copolymer is immobilized on the surface of the membrane matrix through covalent bond.

10. The cation-exchange chromatographic support according to claim 1, wherein the copolymer comprises the (meth)acrylamide-based compound as a hydrophilic monomer unit.

11. The cation-exchange chromatographic support according to claim 1, wherein the copolymer comprises the (meth)acrylate-based compound as a hydrophilic monomer unit.

12. The cation-exchange chromatographic support according to claim 1, wherein the copolymer comprises 2-hydroxyethyl methacrylate as a hydrophilic monomer unit.

13. The cation-exchange chromatographic support according to claim 1, wherein the membrane matrix comprises polyethylene.

14. The cation-exchange chromatographic support according to claim 13, wherein the graft ratio of the copolymer graft-polymerized onto the membrane matrix is 20 to 200%.

15. The cation-exchange chromatographic support according to claim 1, wherein the copolymer substantially has no cross-linked structure.

16. The cation-exchange chromatographic support according to claim 1, wherein the cation-exchange chromatographic support reduces the percentage of aggregates by 50% or more when 100 mg of antibodies including monomers and the aggregates is flow-through purified with respect to 1 mL of the support.

17. A purification method for purifying a physiologically active substance from a mixed solution containing impurities and the physiologically active substance, the purification method comprising contacting the mixed solution with a cation-exchange chromatographic support to obtain the physiologically active substance with improved purity, the cation-exchange chromatographic support comprising a membrane matrix and a copolymer immobilized on the surface of the membrane matrix, wherein the copolymer comprises a (meth)acrylamide-based compound and/or a (meth)acrylate-based compound as monomer units, and the support has one or more species of cation-exchange groups including at least a weak cation-exchange group at a density higher than 30 mmol/L per volume of the support.

18. The purification method according to claim 17, wherein the purification method is based on a flow-through technique.

19. The purification method according to claim 17, wherein the physiologically active substance is a monomer of an antibody protein.

20. The purification method according to claim 17, wherein purification using an anion-exchange chromatographic support is performed before or after the purification step with the cation-exchange chromatographic support.

21. The purification method according to claim 20, wherein buffer replacement is not performed between the purification step with the cation-exchange chromatographic support and the purification step with the anion-exchange chromatographic support.

22. The purification method according to claim 20, wherein the hydrogen ion exponent of the buffer is changed by the addition of an acid or a base between the purification step with the cation-exchange chromatographic support and the purification step with the anion-exchange chromatographic support.

23. The purification method according to claim 17, further comprising a purification step by affinity chromatography before the purification step with the cation-exchange chromatographic support.

24. The purification method according to claim 23, wherein buffer replacement is not performed after elution of the physiologically active substance in the affinity chromatography step.

25. The purification method according to claim 23, wherein the elution buffer for use in the elution of the physiologically active substance in the affinity chromatography step is composed mainly of a monovalent acid.

26. The cation-exchange chromatographic support according to claim 1, wherein the density is higher than 59 mmol/L.

27. The purification method for purifying a physiologically active substance from a mixed solution containing impurities and the physiologically active substance according to claim 17, wherein the physiologically active substance is a biomolecule.

28. The purification method for purifying a physiologically active substance from a mixed solution containing impurities and the physiologically active substance according to claim 27, wherein the biomolecule is an antibody.

29. The cation-exchange chromatographic support according to claim 1, wherein the density is higher than 40 mmol/L.

30. The cation-exchange chromatographic support according to claim 1, wherein the density is higher than 49 mmol/L.

* * * * *